US009611270B2

(12) United States Patent
Aube et al.

(10) Patent No.: US 9,611,270 B2
(45) Date of Patent: Apr. 4, 2017

(54) INHIBITORS OF CYP17A1

(71) Applicant: University of Kansas, Lawrence, KS (US)

(72) Inventors: Jeffrey Aube, Lawrence, KS (US); Emily E. Scott, Lawrence, KS (US); Charlie Fehl, Farmington, MI (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days.

(21) Appl. No.: 14/815,686

(22) Filed: Jul. 31, 2015

(65) Prior Publication Data
US 2016/0031929 A1 Feb. 4, 2016

Related U.S. Application Data

(60) Provisional application No. 62/032,460, filed on Aug. 1, 2014.

(51) Int. Cl.
C07D 487/04 (2006.01)
C07J 73/00 (2006.01)
C07J 71/00 (2006.01)
C07J 43/00 (2006.01)
C07D 401/04 (2006.01)
C07J 31/00 (2006.01)
C07J 21/00 (2006.01)

(52) U.S. Cl.
CPC ......... *C07D 487/04* (2013.01); *C07D 401/04* (2013.01); *C07J 43/003* (2013.01); *C07J 71/001* (2013.01); *C07J 73/005* (2013.01); *C07J 21/008* (2013.01); *C07J 31/006* (2013.01)

(58) Field of Classification Search
CPC .... C07D 487/04; C07D 401/04; C07J 71/001; C07J 73/005; C07J 43/003; C07J 31/006; C07J 21/008
See application file for complete search history.

(56) References Cited

U.S. PATENT DOCUMENTS 5,672,662 A 9/1997 Harris et al.

FOREIGN PATENT DOCUMENTS

WO WO 2009120565 A2 * 10/2009 ............ C07J 43/003

OTHER PUBLICATIONS

Bazin, Marc-Antoine et al., "First synthesis of 7α- and 7β-amino-DHEA, dehydroepiandrosterone (DHEA) analogues and preliminary evaluation of their cytotoxicity on Leydig cells and TM4 Sertoli cells," Bioorg. Med. Chem., (May 1, 2007), vol. 15, Issue 9, pp. 3152-3160.

Beuchet, Pierre et al., "Synthesis of 6(α,β)—aminocholestanols as ergosterol biosynthesis inhibitors," Bioorg. Med. Chem. Lett., (Dec. 15, 1998), vol. 8, Issue 24, pp. 3627-3630.
Dhir, Vivek et al., "Differential Inhibition of CYP17A1 and CYP21A2 Activities by the P450 Oxidoreductase Mutant A287P," Mol. Endocrinology, (2007), vol. 21, Issue 8, pp. 1958-1968.
Imai, Tsuneo et al., "Expression and Purification of Functional Human 17α-Hydroxylase/17,20-Lyase (P450c17) in *Escherichia coli*," J. Biol. Chem., (Sep. 1993), vol. 268, No. 26, pp. 19681-19689.
IUPAC-IUB Joint Commission on Biochemical Nomenclature, "The nomenclature of steroids. Recommendations 1989," Eur. J. Biochem. (1989), vol. 186, Issue 3, pp. 429-458.
Jana, Navendu et. al., "Development of a Suzuki Cross-Coupling Reaction between 2-Azidoarylboronic Pinacolate Esters and Vinyl Triflates to Enable the Synthesis of [2,3]—Fused Indole Heterocycles," J. Org. Chem., (2014), vol. 79, Issue 6, pp. 2781-2791.
Mori, Kenji et al., "Synthesis of some analogues of blattellastanoside A, the steroidal aggregation pheromone of the German cockroach," Bioorg. Med. Chem., (Mar. 1996), vol. 4, Issue 3, pp. 401-408.
Potter, Gerard A. et al., "Novel Steroidal Inhibitors of Human Cytochrome P45017.alpha.-Hydroxylase-C17,20-lyase): Potential Agents for the Treatment of Prostatic Cancer," J. Med. Chem., (1995), vol. 38, Issue 13, pp. 2463-2471.
Roelofs, Maarke J.E. et al., "The relevance of chemical interactions with CYP17 enzyme activity: Assessment using a novel in vitro assay," Toxicol. Appl. Pharmacol., (May 1, 2013), vol. 268, Issue 3, pp. 309-317.

(Continued)

Primary Examiner — Samantha Shterengarts
Assistant Examiner — Matt Mauro
(74) Attorney, Agent, or Firm — Foley & Lardner LLP

(57) ABSTRACT

Compounds according to formula I or II are provided. Such compounds are useful in treating cancers, such as leukemia, colon cancer, breast cancer, or prostate cancer by beneficially inhibiting CYP17A1. Pharmaceutical compositions and methods including the compounds are also provided.

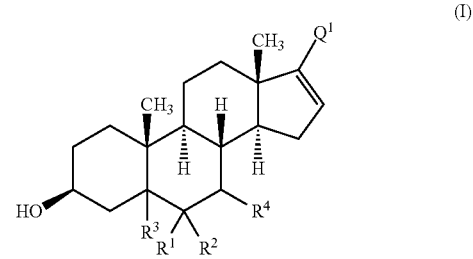

(I)

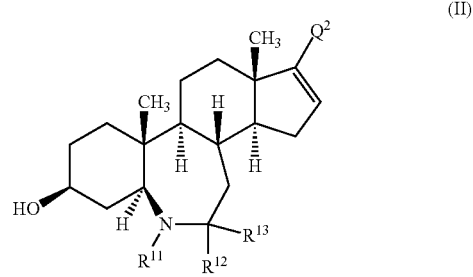

(II)

22 Claims, No Drawings

(56) References Cited

OTHER PUBLICATIONS

Sandee, Duanpen et al., "High-Yield Expression of a Catalytically Active Membrane-Bound Protein: Human P450 Oxidoreductase," Endocrinology, (2011), vol. 152, No. 7, pp. 2904-2908.

Yamaoka, Masuo et al., "Orteronel (TAK-700), a novel non-steroidal 17,20-lyase inhibitor: Effects on steroid synthesis in human and monkey adrenal cells and serum steroid levels in cynomolgus monkeys," J. of Steriod Biochem. and Mol. Biology, (Apr. 2012), vol. 129, Issues 3-5, pp. 115-128.

* cited by examiner

INHIBITORS OF CYP17A1

CROSS-REFERENCE TO RELATED PATENT APPLICATIONS

This application claims priority to U.S. Provisional Patent Application No. 62/032,460, filed Aug. 1, 2014, the entire disclosure of which is hereby incorporated by reference in their entireties for any and all purposes.

GOVERNMENT RIGHTS

This invention was made with government support under R01-GM102505 and T32-GM08545 awarded by the National Institutes of Health. The government has certain rights in the invention.

FIELD

Compounds and compositions are disclosed that are useful in treating cancers, such as leukemia, colon cancer, breast cancer, or prostate cancer. The compounds beneficially inhibit CYP17A1.

SUMMARY

In an aspect, a compound according to formula I or II is provided

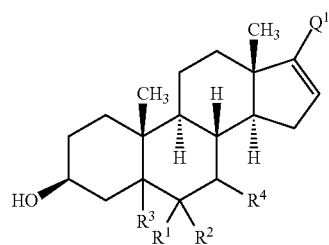

(I)

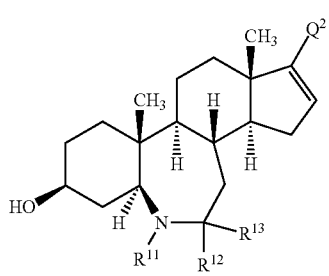

(II)

or a salt thereof, or a tautomer thereof, or a solvate thereof.
In formula I or II,
$Q^1$ is

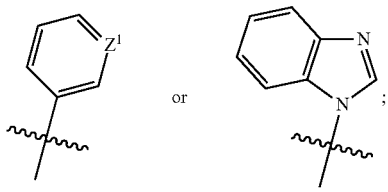

$Q^2$ is

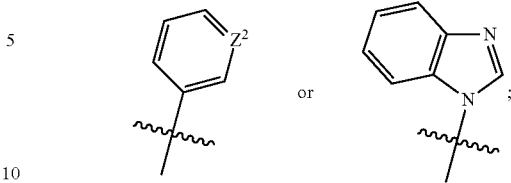

$R^1$ and $R^2$ are each independently H, OH, $C(O)NR^{27}R^5$, $C(O)OR^6$, $NR^7R^8$, trifluoromethyl, trifluoromethoxy, halo, nitro, cyano, or a substituted or unsubstituted alkoxy, aryloxy, arylalkoxy, or alkanoyloxy group provided that $R^1$ and $R^2$ are not both H, or $R^1$ and $R^2$ together are =O, =N—OH, =N—NHR$^9$; $R^3$ is H, or $R^1$ and $R^3$ together are O, NR$^9$, S, S(O), S(O)$_2$, or a bond, provided that when $R^1$ and $R^3$ together are not NR$^9$ or a bond then $R^2$ is not NR$^7R^8$; $R^4$ is H, or $R^1$ and $R^4$ together are O, NR$^{10}$, S, S(O), S(O)$_2$, or a bond, provided that when $R^1$ and $R^3$ together are not NR$^{10}$ or a bond then $R^2$ is not NR$^7R^8$; $Z^1$ and $Z^2$ are each independently CH or N; $R^{27}$, $R^5$, $R^7$, $R^8$, $R^9$, and $R^{10}$ are each independently H or a substituted or unsubstituted alkyl, cycloalkyl, cycloalkylalkyl, alkanoyl, aryl, aralkyl, heterocyclyl, heteroaryl, heterocyclylalkyl, or heteroaralkyl group; $R^6$ is independently at each occurrence H or a substituted or unsubstituted alkyl, cycloalkyl, cycloalkylalkyl, aryl, aralkyl, heterocyclyl, heteroaryl, heterocyclylalkyl, or heteroaralkyl group; $R^{11}$ is H or a substituted or unsubstituted cycloalkyl, cycloalkylalkyl, alkanoyl, aryl, aralkyl, heterocyclyl, heteroaryl, heterocyclylalkyl, or heteroaralkyl group; $R^{12}$ and $R^{13}$ are each H or together are =O, provided that $R^{12}$ and $R^{13}$ together are not =O when $R^{11}$ is H; or $R^{11}$, $R^{12}$, and $R^{13}$ together are —N=N—N=. In such compounds, where $Z^1$ is N, $R^1$ and $R^3$ together are a bond, and $R^4$ is H, then $R^2$ is not H.

Pharmaceutical compositions and methods including compounds of formulas I and II are also provided.

DETAILED DESCRIPTION

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡$CCH_3$, —$CH_2$C≡$CCH_3$, —C≡$CCH_2$CH($CH_2CH_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)— alkyl groups and —O—C(O)— alkyl groups, each containing 2-5 carbon atoms.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group.

The term "ester" as used herein refers to —COOR$^{30}$ groups. R$^{30}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{31}$R$^{32}$, and —NR$^{31}$C(O)R$^{32}$ groups, respectively. R$^{31}$ and R$^{32}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{31}$C(O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{33}$C(O)OR$^{34}$ and —OC(O)NR$^{33}$R$^{34}$ groups, respectively. R$^{33}$ and R$^{34}$ are independently a substituted or unsubstituted alkyl, alkenyl, alkynyl, cycloalkyl, aryl, aralkyl, heterocyclylalkyl, or heterocyclyl group as defined herein. R$^{33}$ may also be H.

The term "amine" (or "amino") as used herein refers to —NR$^{35}$R$^{36}$ groups, wherein R$^{35}$ and R$^{36}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{38}$R$^{39}$ and —NR$^{38}$SO$_2$R$^{39}$ groups, respectively. R$^{38}$ and R$^{39}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "halogen" or "halo" as used herein refers to bromine, chlorine, fluorine, or iodine. In some embodiments, the halogen is fluorine. In other embodiments, the halogen is chlorine or bromine.

The term "hydroxy' as used herein can refer to —OH or its ionized form, —O$^-$.

The term "nitro" as used herein refers to an —NO$_2$ group.

The term "trifluoromethyl" as used herein refers to —CF$_3$.

The term "trifluoromethoxy" as used herein refers to —OCF$_3$.

The phrase "selectively inhibits" as used herein will be understood by persons of ordinary skill in the art and will vary to some extent depending upon the context in which the phrase is used. If there are uses of the phrase which are not clear to persons of ordinary skill in the art, given the context in which the phrase is used, the phrase at minimum refers to the compounds acting through an enzyme-specific mechanism of action, resulting in fewer off-target effects because the compounds target a particular enzyme over other potential enzymes. The phrase may further be modified as discussed herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

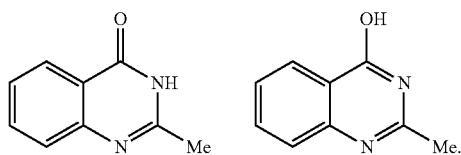 [SMILES: Cc1nc2ccccc2c(=O)[nH]1 ; Cc1nc(O)c2ccccc2n1]

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Agents that block the production of various hormones are well-validated therapies for many indications, including cancer, cardiology, inflammation, and the effects of diabetes. Such therapies ideally use an agent that is selective for an intended target in a designated biosynthetic pathway. Undesired effects can arise if related but unintended pathways become affected. For example, elevated levels of circulating glucocorticoids are associated with the development of severe adverse effects such as insulin resistance, dyslipidemia, and central adiposity, all characteristics related to the onset of type 2 diabetes.

Several major classes of hormones contain the steroid nucleus. Steroid hormones are involved in a diverse array of metabolic, homeostatic, and neurologic processes, as well as cellular growth and development. From an oncologic perspective, if certain biological processes that initiate growth or metabolic enhancement become overactive, carcinogenesis and/or tumor growth may occur. In several cases, such tumors remain dependent on these signals, creating an opportunity for therapeutic intervention. For example, agents that block sex steroidogenesis are recognized candidates for treating breast and prostate cancers, which derive from sex steroid-responsive tissues.

Several of the enzymes involved in steroid biosynthesis belong to the cytochrome P450 superfamily. The members of the cytochrome P450 superfamily, generally referred to as P450 enzymes, are heme-containing monooxygenases that are membrane-bound in humans. P450 enzymes are categorized into individual families, subfamilies, and enzymes based on amino acid sequence identity. For example, CYP17A1 is classified as cytochrome P450 family 17, subfamily A, enzyme 1. The overall tertiary structure of P450 enzymes, colloquially referred to as the P450 fold, is highly conserved across all members of the superfamily. Another common feature of human P450 enzymes is that they are usually localized in the membranes of the endoplasmic reticulum or mitochondria. This co-localizes human P450 enzymes with their redox partner protein, NADPH-cytochrome P450 oxidoreductase (POR), which reduces the substrate-heme complex to advance the catalytic cycle.

P450 enzymes can be loosely generalized into xenobiotic-metabolizing enzymes and enzymes involved in endogenous metabolism. The xenobiotic class typically oxidizes hydrophobic substrates to more hydrophilic metabolites, which are more readily excreted from the system. Although this metabolism is an essential aspect of drug use, it may lead to serious concerns in pharmacotherapy. For example, drug-drug interactions or the oxidation to a reactive metabolite can cause drug-based toxicities. These enzymes typically bind and oxidize multiple chemicals with diverse substitution. In contrast, P450 enzymes associated with endogenous metabolism are often involved in the highly specific synthesis of a bioactive molecule. Some P450 enzymes carry out both functions, such as CYP1A2, which metabolizes many drugs in addition to estrogen hormones.

CYP17A1 is a member of the endogenous biosynthetic group, and typically accepts only four very similar endogenous substrates: pregnenolone, progesterone, and their respective 17α-hydroxylated versions. Compounds that target CYP17A1 may be used as therapeutics for cancers, especially breast and prostate cancers.

In addition, CYP21A2 has been found to be a potential off-target of CYP17A1 inhibitors. CYP21A2 activity is required for corticosteroid production and is involved in mineralocorticoid production and blood pressure regulation. Thus, while less selective CYP17A1 inhibitors may be used as therapeutic agents, providing CYP17A1 inhibitors with enhanced CYP17A1 selectivity over CYP21A2 is especially beneficial.

The present technology provides compounds that beneficially inhibit CYP17A1. Moreover, many of these compounds are selective for CYP17A1 over CYP21A2. Accordingly, in an aspect, a compound according to formula I or II is provided

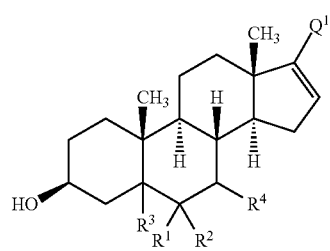
(I)

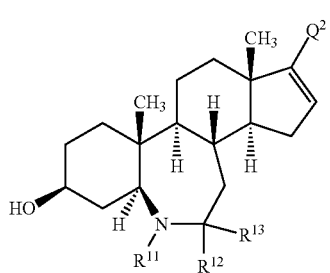
(II)

or a salt thereof, or a tautomer thereof, or a solvate thereof. In formula I or II,
$Q^1$ is

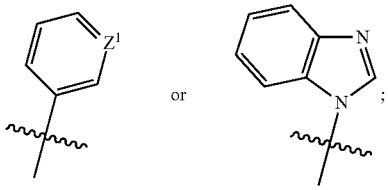

$Q^2$ is

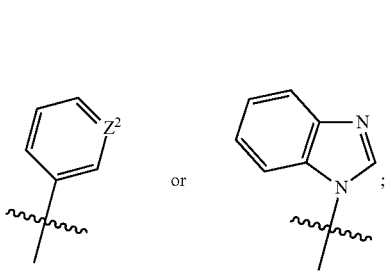

$R^1$ and $R^2$ are each independently H, OH, $C(O)NR^{27}R^5$, $C(O)OR^6$, $NR^7R^8$, trifluoromethyl, trifluoromethoxy, halo, nitro, cyano, or a substituted or unsubstituted alkoxy, aryloxy, arylalkoxy, or alkanoyloxy group provided that $R^1$ and $R^2$ are not both H, or $R^1$ and $R^2$ together are =O, =N—OH, =N—$NHR^9$; $R^3$ is H, or $R^1$ and $R^3$ together are O, $NR^9$, S, S(O), $S(O)_2$, or a bond, provided that when $R^1$ and $R^3$ together are not $NR^9$ or a bond then $R^2$ is not $NR^7R^8$; $R^4$ is H, or $R^1$ and $R^4$ together are O, $NR^{10}$, S, S(O), $S(O)_2$, or a bond, provided that when $R^1$ and $R^3$ together are not $NR^{10}$ or a bond then $R^2$ is not $NR^7R^8$; $Z^1$ and $Z^2$ are each independently CH or N; $R^{27}$, $R^5$, $R^7$, $R^8$, $R^9$, and $R^{10}$ are each independently H or a substituted or unsubstituted alkyl, cycloalkyl, cycloalkylalkyl, alkanoyl, aryl, aralkyl, heterocyclyl, heteroaryl, heterocyclylalkyl, or heteroaralkyl group; $R^6$ is independently at each occurrence H or a substituted or unsubstituted alkyl, cycloalkyl, cycloalkylalkyl, aryl, aralkyl, heterocyclyl, heteroaryl, heterocyclylalkyl, or heteroaralkyl group; $R^{11}$ is H or a substituted or unsubstituted cycloalkyl, cycloalkylalkyl, alkanoyl, aryl, aralkyl, heterocyclyl, heteroaryl, heterocyclylalkyl, or heteroaralkyl group; $R^{12}$ and $R^{13}$ are each H or together are =O, provided that $R^{12}$ and $R^{13}$ together are not =O when $R^{11}$ is H; or $R^{11}$, $R^{12}$, $R^{13}$ together are —N=N—N=. In such compounds, where $Z^1$ is N, $R^1$ and $R^3$ together are a bond, and $R^4$ is H, then $R^2$ is not H. In some embodiments, $Z^1$ and $Z^2$ are each N.

The compound of formula I may be a compound according to formula Ia or Ib:

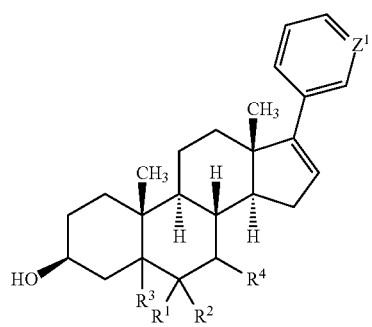
(Ia)

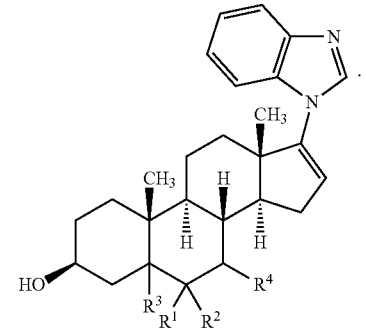
(Ib)

The compound of formula II may be a compound of formula IIa or IIb:

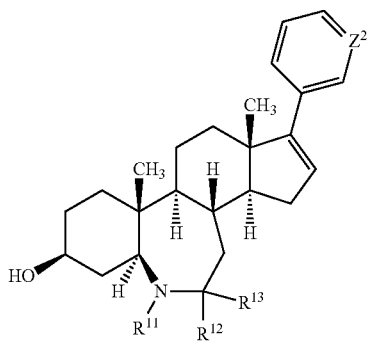
(IIa)

(IIb)

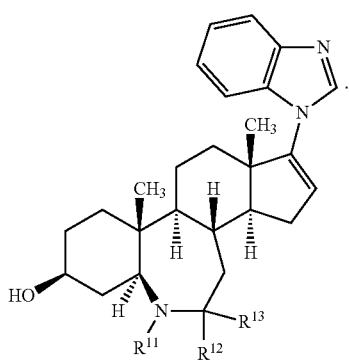

The compound of formula I may be a compound according to formulas III, IV, or V (III)

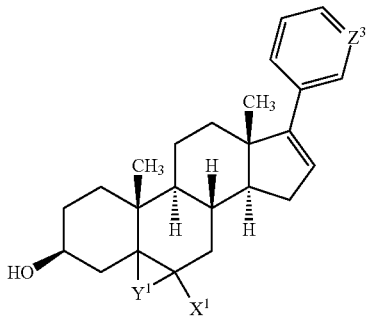

(IV)

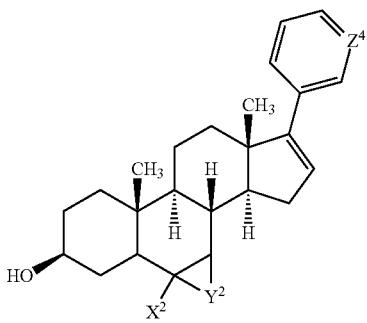

(V)

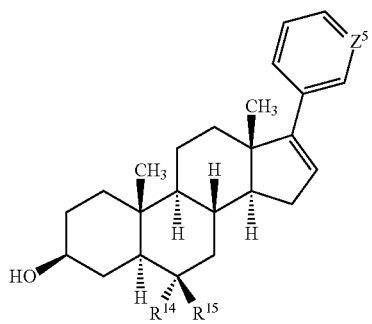

or a salt thereof, or a tautomer thereof, or a solvate thereof.

In formulas III, IV, or V, $X^1$ and $X^2$ are each independently H, $C(O)NR^{16}R^{17}$, $C(O)OR^{18}$, $NR^{19}R^{20}$, trifluoromethyl, halo, nitro, or cyano; $Y^1$ and $Y^2$ are each independently O, $NR^{21}$, S, S(O), $S(O)_2$, or a bond, provided that when $Y^1$ and $Y^2$ are not $NR^{21}$ or a bond then $X^1$ and $X^2$ are not $NR^{19}R^{20}$; $Z^3$, $Z^4$, and $Z^5$ are each independently CH or N; $R^{14}$ and $R^{15}$ are each independently H, OH, $NR^{22}R^{23}$, trifluoromethoxy, or a substituted or unsubstituted alkoxy, aryloxy, arylalkoxy, or alkanoyloxy, group provided that $R^{14}$ and $R^{15}$ are not both H, or $R^{14}$ and $R^{15}$ together are =O, =N—OH, or =N—NHR$^{24}$; $R^{16}$; $R^{17}$, $R^{19}$; $R^{20}$, $R^{21}$, $R^{22}$, $R^{23}$ and $R^{24}$ are each independently H or a substituted or unsubstituted alkyl, cycloalkyl, cycloalkylalkyl, alkanoyl, aryl, aralkyl, heterocyclyl, heteroaryl, heterocyclylalkyl, or heteroaralkyl group; and $R^{18}$ is H or a substituted or unsubstituted alkyl, cycloalkyl, cycloalkylalkyl, aryl, aralkyl, heterocyclyl, heteroaryl, heterocyclylalkyl, or heteroaralkyl group. It is to be understood that in formula III, when $Z^3$ is N and $Y^1$ is a bond then $X^1$ is not H. In some embodiments, $Z^3$, $Z^4$, and $Z^5$ are each independently N. In some embodiments, $Y^1$ is O or a bond; $Y^2$ is a bond; and $X^1$ and $X^2$ are each independently $C(O)NR^{16}R^{17}$, $C(O)OR^{18}$, $NR^{19}R^{20}$, nitro, or cyano. In some embodiments, $R^{14}$ and $R^{15}$ are each independently H, OH, $NR^{22}R^{23}$, trifluoromethoxy; or $R^{14}$ and $R^{15}$ together are =O or =N—OH.

In some embodiments, the compound of formula II is a compound of formula VI, VII, or VIII (VI)

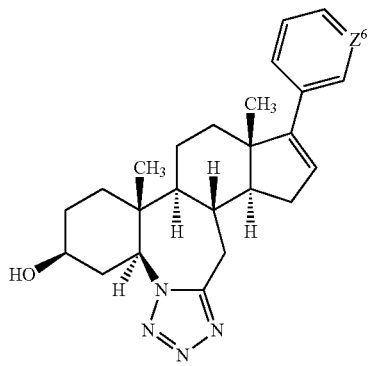

(VII)

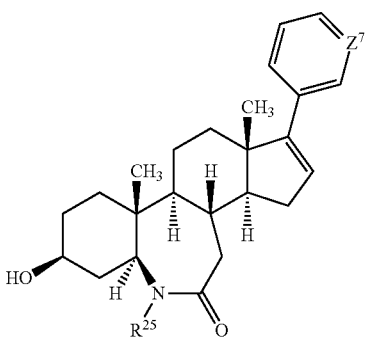

(VIII)

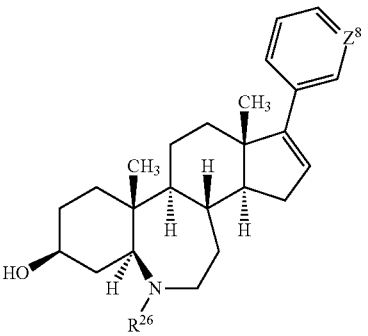

or a salt thereof, or a tautomer thereof, or a solvate thereof, where $Z^6$, $Z^7$, and $Z^8$ are each independently CH or N; $R^{25}$ is H or a substituted or unsubstituted cycloalkyl, cycloalkylalkyl, alkanoyl, aryl, aralkyl, heterocyclyl, heteroaryl, heterocyclylalkyl, or heteroaralkyl group; and $R^{26}$ is a substituted or unsubstituted cycloalkyl, cycloalkylalkyl, alkanoyl, aryl, aralkyl, heterocyclyl, heteroaryl, heterocyclylalkyl, or heteroaralkyl group. Formula VI is an example of where $R^{11}$, $R^{12}$, and $R^{13}$ together are —N=N—N= in formula II.

Exemplary compounds of the present technology include, but are not limited to,

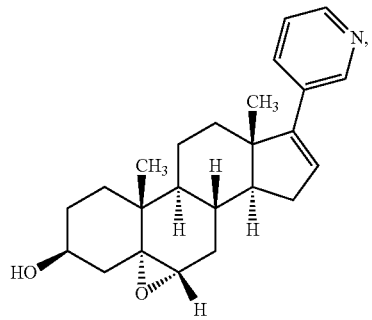

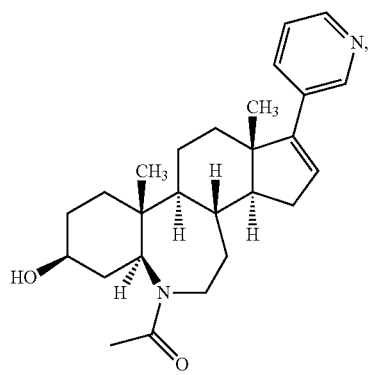

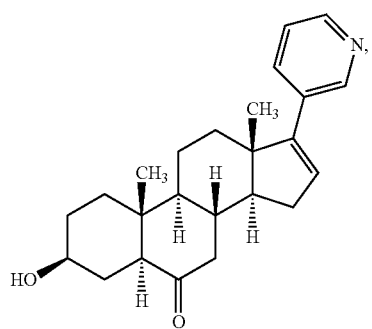

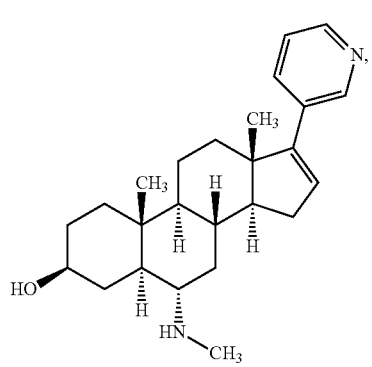

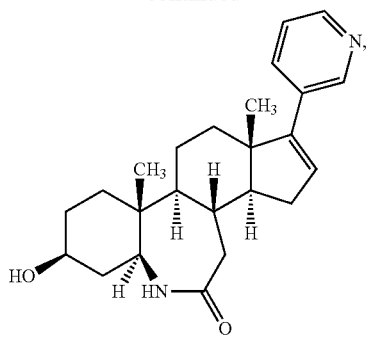

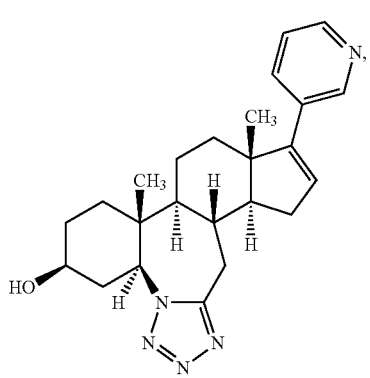

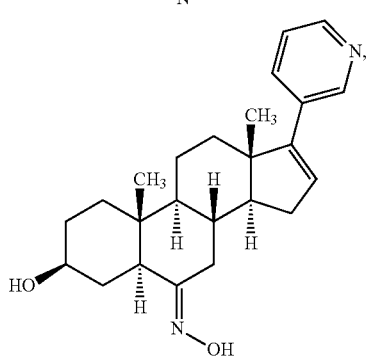

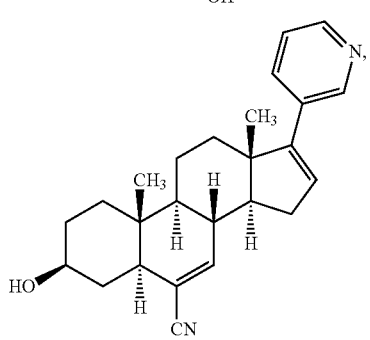

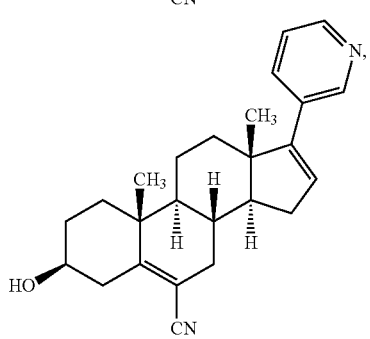

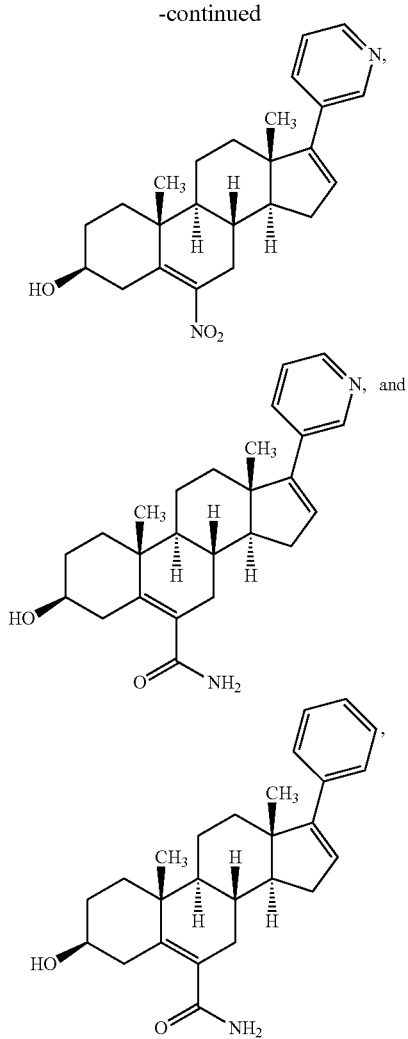

as well as salts thereof, tautomers thereof, or solvates thereof of any of these.

In an aspect of the present technology, a composition is provided that includes any one of the embodiments of compounds of formulas I, Ia, Ib, II, IIa, IIb, III, IV, V, VI, VII, or VIII (or a salt thereof, or a tautomer thereof, or a solvate thereof) and a pharmaceutically acceptable carrier. In a related aspect, a pharmaceutical composition for treating a condition is provided, the pharmaceutical composition including a therapeutically effective amount of the compound of any one of the embodiments of formulas I, Ia, Ib, II, IIa, IIb, III, IV, V, VI, VII, or VIII (or a salt thereof, or a tautomer thereof, or a solvate thereof); and where the condition is leukemia, colon cancer, breast cancer, or prostate cancer. In a further related aspect, a method is provided that includes administering a therapeutically effective amount of a compound of any one of the embodiments of formulas I, Ia, Ib, II, IIa, IIb, III, IV, V, VI, VII, or VIII or administering a pharmaceutical composition comprising a therapeutically effective amount of a compound of any one of the embodiments of formulas I, Ia, Ib, II, IIa, IIb, III, IV, V, VI, VII, or VIII to a subject suffering from leukemia, colon cancer, breast cancer, or prostate cancer.

"Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of cancer such as leukemia, colon cancer, breast cancer, or prostate cancer. Another example of an effective amount includes amounts or dosages that are capable of reducing symptoms associated with cancers, such as, for example, leukemia, colon cancer, breast cancer, or prostate cancer. In some embodiments, the compound selectively inhibits CYP17A1. In some embodiments, the compound selectively inhibits CYP17A1 at least 5 times more, at least 10 times more, at least 25 times more, or at least 50 times more than CYP21A2. In some embodiments, the effective amount of the compound selectively inhibits CYP17A1. In some embodiments, the effective amount of the compound selectively inhibits CYP17A1 at least 5 times more than CYP21A2. In some embodiments, the effective amount of the compound selectively inhibits CYP17A1 at least 10 times more than CYP21A2. In some embodiments, the effective amount of the compound selectively inhibits CYP17A1 at least 25 times more than CYP21A2. In some embodiments, the effective amount of the compound selectively inhibits CYP17A1 at least 50 times more than CYP21A2. In any of the above embodiments, it may be the compound or the effective amount of the compound selectively inhibits CYP17A1 hydroxylase activity over CYP21A2 hydroxylase activity. In any of the above embodiments, it may be the compound or the effective amount of the compound selectively inhibits CYP17A1 progesterone 17α-hydroxylation activity over CYP21A2 progesterone 21-hydroxylation activity. As used herein, a "subject" or "patient" is a mammal, such as a cat, dog, rodent or primate. Typically the subject is a human, and, preferably, a human suffering from or suspected of suffering from a cancer such as breast cancer or prostate cancer. The term "subject" and "patient" can be used interchangeably.

Thus, the instant present technology provides pharmaceutical compositions and medicaments comprising any of the compounds disclosed herein (e.g., compounds of formulas I, Ia, Ib, II, IIa, IIb, III, IV, V, VI, VII, or VIII) and a pharmaceutically acceptable carrier or one or more excipients or fillers. The compositions may be used in the methods and treatments described herein. Such compositions include an effective amount of any compound as described herein, including but not limited to a compound of formula I or II. The pharmaceutical composition may be packaged in unit dosage form. The unit dosage form is effective in treating a cancer by reducing the viability of cancerous cells and/or reducing the size of a tumor when administered to a subject in need thereof.

The pharmaceutical compositions may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like to prevent and treat leukemia, colon cancer, breast cancer, or prostate cancer. The compounds and compositions described herein may be used to prepare formulations and medicaments that prevent or treat a variety of disorders associated with leukemia, colon cancer, breast cancer, or prostate cancer. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or antioxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until, for example, a reduction of symptoms and/or (for a subject with a cancer) a reduction in the viability of cancerous cells and/or tumor size is observed. The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

Effectiveness of the compositions and methods of the present technology may also be demonstrated by a decrease in the symptoms of a cancer, such as, for example, a reduction in tumor size. Effectiveness of the compositions and methods of the present technology may also be demonstrated by a decrease in the symptoms of leukemia, colon cancer, breast cancer, or prostate cancer.

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

In one aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1\times10^{-4}$ g/kg to 1 g/kg, preferably, $1\times10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkylene glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

In an aspect, a method is provided that includes inhibiting CYP17A1 by administration of a compound of formula I, Ia, Ib, II, IIa, IIb, III, IV, V, VI, VII, or VIII (or a salt thereof, or a tautomer thereof, or a solvate thereof), or by administration of a pharmaceutical composition of a compound of formula I, Ia, Ib, II, IIa, IIb, III, IV, V, VI, VII, or VIII. It may be that the administration of the compound or pharmaceutical composition selectively inhibits CYP17A1, e.g., by selectively inhibiting CYP17A1 over CYP21A2. In some embodiments, the compound or pharmaceutical composition selectively inhibits CYP17A1 at least 5 times more than CYP21A2. In some embodiments, the compound or pharmaceutical composition selectively inhibits CYP17A1 at least 10 times more than CYP21A2. In some embodiments, the compound or pharmaceutical composition selectively inhibits CYP17A1 at least 25 times more than CYP21A2. In some embodiments, the compound or pharmaceutical composition selectively inhibits CYP17A1 at least 50 times more than CYP21A2. In any of the above embodiments, it may be the compound or pharmaceutical composition selectively inhibits CYP17A1 hydroxylase activity over CYP21A2 hydroxylase activity. In any of the above embodiments, it may be the compound or the effective amount of the compound selectively inhibits CYP17A1 progesterone 17α-hydroxylation activity over CYP21A2 progesterone 21-hydroxylation activity.

In an aspect, a method of preventing or treating a biological condition is provided that includes administering to a subject suffering from a biological condition selected from leukemia, colon cancer, breast cancer, or prostate cancer, an effective amount of a compound of formula I, Ia, Ib, II, IIa, IIb, III, IV, V, VI, VII, or VIII (or a salt thereof, or a tautomer thereof, or a solvate thereof) or a pharmaceutical composition including an effective amount of a compound of formula I, Ia, Ib, II, IIa, IIb, III, IV, V, VI, VII, or VIII (or a salt thereof, or a tautomer thereof, or a solvate thereof). The effective amount of the compound may selectively inhibit CYP17A1 at least 5 times more than CYP21A2. The effective amount of the compound may selectively inhibit CYP17A1 at least 10 times more, at least 35 times more, or at least 50 times more than CYP21A2. In any of the above embodiments, it may be the effective amount of the compound selectively inhibits CYP17A1 hydroxylase activity over CYP21A2 hydroxylase activity. In any of the above embodiments, it may be the effective amount of the compound selectively inhibits CYP17A1 progesterone 17α-hydroxylation activity over CYP21A2 progesterone 21-hydroxylation activity.

In a related aspect, a method of preventing or treating a biological condition is provided that includes administering to a subject suffering from a biological condition selected from leukemia, colon cancer, breast cancer, or prostate cancer, a pharmaceutical composition that includes an effective amount of the compound of formula I, Ia, Ib, II, IIa, IIb, III, IV, V, VI, VII, or VIII (or a salt thereof, or a tautomer thereof, or a solvate thereof). In any of the above embodiments, it may be the compound or an effective amount of the compound selectively inhibits CYP17A1 hydroxylase activity over CYP21A2 hydroxylase activity. In any of the above embodiments, it may be the compound or an effective amount of the compound selectively inhibits CYP17A1 progesterone 17α-hydroxylation activity over CYP21A2 progesterone 21-hydroxylation activity.

In another aspect, the present technology provides methods of identifying a target of interest including contacting the target of interest with a detectable or imaging effective quantity of a labeled compound of the present technology. A detectable or imaging effective quantity is a quantity of a labeled compound of the present technology necessary to be detected by the detection method chosen. For example, a detectable quantity can be an administered amount sufficient to enable detection of binding of the labeled compound to a target of interest including, but not limited to, a CYP17A1. Suitable labels are known by those skilled in the art and can include, for example, radioisotopes, radionuclides, isotopes, fluorescent groups, biotin (in conjunction with streptavidin complexation), and chemoluminescent groups. Upon binding of the labeled compound to the target of interest, the target may be isolated, purified and further characterized such as by determining the amino acid sequence.

The terms "associated" and/or "binding" can mean a chemical or physical interaction, for example, between a compound of the present technology and a target of interest. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds of the present technology can bind to or interact with a target of interest or precursors, portions, fragments and peptides thereof and/or their deposits.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

General synthetic and analytical details: $^1$H and $^{13}$C NMR spectra were collected on a Bruker DRX-400 (400 MHz and 100 MHz, respectively) or a Bruker AM-500 (500 MHz and 125 MHz, respectively) instrument. Unless otherwise noted, all samples were dissolved in CDCl$_3$. A drop of MeOD was sometimes added to aid solubility. All chemical shifts are expressed in parts per million (δ) relative to residual CHCl$_3$ as an internal standard (δ 7.27 ppm $^1$H NMR, 77.35 ppm $^{13}$C NMR). Abbreviations are: s, singlet; d, doublet; t, triplet, q, quartet; m, multiplet; dd, doublet of doublets; qd, quartet of doublets; td, triplet of doublets. The infrared (IR) spectra were recorded on Perkin-Elmer 1420 spectrometer or a Perkin-Elmer Spectrum One FT-IR and the absorption frequencies are reported in cm$^{-1}$. Low resolution mass spectra (MS) and high resolution mass spectra (HRMS) were recorded on a Waters LCT Premier TOF spectrometer for electrospray ionization (ESI) or a VG Instrument ZAB double-focusing mass spectrometer (FAB). Parallel Evaporations were performed using a GeneVac EZ-2 plus evaporator. Automated preparative reverse-phase HPLC purification was performed using a Waters 2767 Mass Directed Fractionation system (2767 sample manager, 2525 Binary Pump, 515 Make-up pump) with a Waters ZQ quadrapole spectrometer and detected by UV (270 nm, Waters Xterra MS C-18 column, 19×150 mm, elution with the appropriate gradient of acetonitrile in pH 9.8 buffered aqueous ammonium formate at 18 mLmin-1 flow rate). Purity was determined by reverse-phase HPLC with peak area (UV) at 214 nm using a Waters Alliance 2795 system (Waters Xterra MS C-18 column, 4.6×150 mm, elution with a linear gradient of 5% acetonitrile in pH 9.8 buffered aqueous ammonium formate to 100% acetonitrile at 1.0 mLmin-1 flow rate). Flash chromatography was performed using Sorbent technologies silica gel (32-63 mesh) with the reported eluent system. Automated purification was performed on a Combiflash Rf (Teledyne Isco, Lincoln, Nebr.). Acetonitrile, methylene chloride and THF were dried by passing through two packed columns of neutral alumina using the PurSolv solvent purification system (Innovative Technology Inc.) prior to use. All chemicals were used as purchased from commercial suppliers. Dry flasks (noted) were baked in an oven overnight or were flame dried under vacuum and then placed under a positive pressure of argon. Microwave reactions were conducted with a Biotage Initiator instrument. Automated purification was performed using a Combiflash Rf 200 (Teledyne Isco, Lincoln, Nebr.). Photochemistry was performed in a Rayonet RPR-100 reactor equipped with RPR-3000 lamps, λ$_{max}$ 305 nm (Southern New England Ultraviolet Company, Branford, Conn.). Microwave reactions were carried out in a Biotage Initiator (Biotage USA, Charlotte, N.C.).

A simplified steroid naming convention is used for certain compounds below, as described in IUPAC-IUB Joint Commission on Biochemical Nomenclature (JCBN), "The nomenclature of steroids. Recommendations 198," Eur. J. Biochem. 1989, 186, 429-458. Steroid substitution will be indicated according to the numbering shown in Scheme 1.

Scheme 1.

Androstane numbering

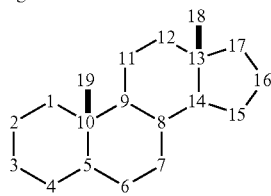

6a-Aza-6a-homosteroid

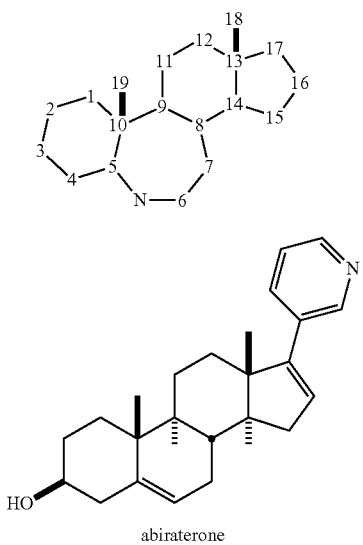

abiraterone

For example, 17-(3-pyridyl)-androst-5,16-dien-3β-ol will correspond to the structure of abiraterone (5).

Exemplary Synthesis and Characterization

3β-Acetoxy-androst-5-en-17-one (2)

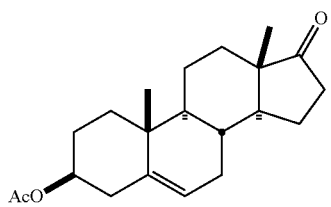

Dehydroepiandrosterone 1 (10.0 g, 34.7 mmol) was added to a dry 20 mL microwave vial as a fine powder. Toluenesulfonic acid (0.066 g, 0.35 mmol) was added as a solid, and the mixture suspended in acetic anhydride (13.1 mL, 138 mmol). Microwave irradiation was applied to 80° C. for 6 min. Upon cooling, the resulting wet solid was dissolved in 200 mL methylene chloride, and 200 mL of a saturated aqueous solution of sodium bicarbonate was slowly added. This mixture was stirred overnight. The organic layer was separated, followed by further extraction with two portions of methylene chloride. The pooled organic layers were washed with brine, dried over sodium sulfate, and concentrated, affording 11.3 g (98% crude yield) as a white crystalline solid. The analytical data matched reported values, such as in Bazin, M.-A.; Travert, C.; Carreau, S.; Rault, S.; Kihel, L. E. First synthesis of 7α- and 7β-amino-DHEA, dehydroepiandrosterone (DHEA) analogues and preliminary evaluation of their cytotoxicity on Leydig cells and TM4 Sertoli cells. *Bioorg. Med. Chem.* 2007, 15, 3152-3160.

3β-Acetoxy-17-triflyl-androst-5,16-diene (3)

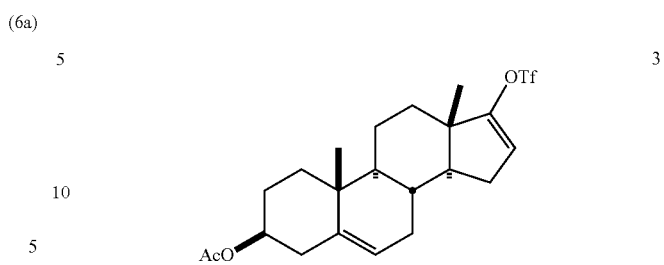

Compound 2 (11.3 g, 34.1 mmol) was added to a dry 500 mL round bottom flask and dissolved in dry methylene chloride (227 mL, 0.15 M). The solution was cooled to −78° C., and 2,6-lutidine (8.1 mL, 70.0 mmol) was added. Triflic anhydride (10.5 mL, 61.1 mmol) was added over 30 min. The solution was stirred at −78° C. for 2 h, then was allowed to age at −20° C. (freezer) overnight. When cold, the reaction was worked up with 1.0 N HCl (100 mL), extracted with methylene chloride, and dried over brine and sodium sulfate. The organic layer was concentrated onto silica and purified by silica chromatography (60 g silica, 0% to 5% to 10% ethyl acetate/hexanes) to obtain 12.3 g of a pale yellow solid (79%). The analytical data matched reported values, such as in Jana, N.; Nguyen, Q.; Driver, T. G. Development of a Suzuki Cross-Coupling Reaction between 2-Azidoarylboronic Pinacolate Esters and Vinyl Triflates To Enable the Synthesis of [2,3]-Fused Indole Heterocycles. *J. Org. Chem.* 2014, 79, 2781-2791.

3β-Acetoxy-17-(3-pyridyl)-andro-5,16-diene (4, abiraterone acetate)

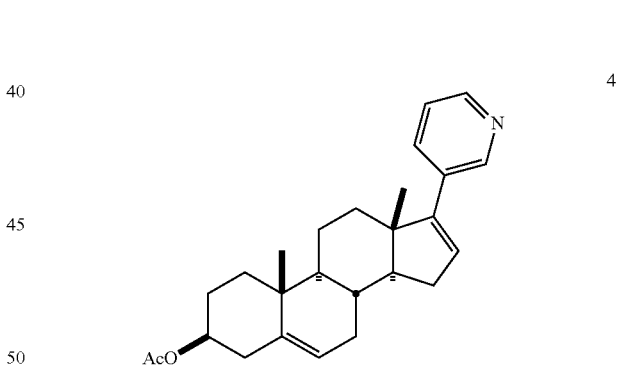

Compound 3 (2 g, 4.3 mmol) was added to a round-bottomed flask and dissolved in a mixture of THF (29 mL, 0.15 M) and saturated aqueous sodium bicarbonate (8.6 mL, ~8.6 mmol). Bis(triphenylphosphine)palladium(II) dichloride (301 mg, 0.43 mmol) and diethyl (3-pyridyl)borane (691 mg, 4.73 mmol) were added. A condenser was attached, and the mixture heated to 60° C. for 1 h. The THF was removed under an $N_2$ stream, and water was added. The mixture was extracted with chloroform, washed with brine, and dried over $NaSO_4$. The crude material was purified by automatic purification (40 g silica, 10% to 30% to 50% EtOAc/hexanes) to yield 1.63 g of white solid (94%). The analytical data matched reported values, such as in Potter, G. A.; Barrie, S. E.; Jarman, M.; Rowlands, M. G. Novel Steroidal Inhibitors of Human Cytochrome P45017.alpha.-

Hydroxylase-C17,20-lyase): Potential Agents for the Treatment of Prostatic Cancer. *J. Med. Chem.* 1995, 38, 2463-2471.

17-(3-Pyridyl)-androst-5,16-dien-3β-ol (5, abiraterone)

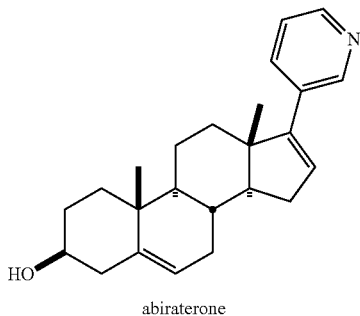

abiraterone

Compound 4 (150 mg, 0.382 mmol) was dissolved in methanol (12.7 mL, 0.03 M). Solid potassium carbonate (422 mg, 3.06 mmol) was added, and the mixture stirred at rt overnight. The mixture was brought to pH~9 with aqueous 1 N HCl and extracted with chloroform. The organic phases were washed with brine and dried over NaSO4. The crude material was purified by automatic purification (25% to 50% EtOAc/hexanes) to isolate 103 mg as a white solid (77%). The analytical data matched reported values, such as in Potter, G. A.; Barrie, S. E.; Jarman, M.; Rowlands, M. G. Novel Steroidal Inhibitors of Human Cytochrome P45017.alpha.-Hydroxylase-C17,20-lyase): Potential Agents for the Treatment of Prostatic Cancer. *J. Med. Chem.* 1995, 38, 2463-2471.

3β-Acetoxy-5α,6α-epoxy-17-triflyl-androst-16-ene (6) and isomer

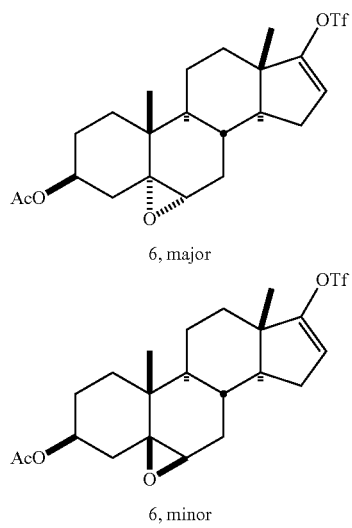

Compound 3 (500 mg, 0.214 mmol) was dissolved in dry methylene chloride (2.1 mL, 0.1 M) and cooled to 0° C. Chloroperoxybenzoic acid (77% pure, 240 mg, 0.214 mmol) was added and the mixture stirred overnight, warming to rt. Saturated aqueous sodium bicarbonate (2 mL) was added and the mixture stirred for 1 h at rt. The mixture was extracted twice more with methylene chloride, washed with brine, and dried over NaSO4. The crude material was purified by automatic purification (4 g silica, 10% to 20% ethyl acetate/hexanes) to obtain 100 mg (92%) of a white solid. $^1$H NMR showed the isolate to be a ca. 7:3 mixture of the 5α,6α:5β,6β-epoxide isomers. The major diastereomeric isomer was established by analogy to the related mixture observed upon mCPBA epoxidation at this position (see Mori, K.; Nakayama, T.; Sakuma, M. Synthesis of some analogues of blattellastanoside A, the steroidal aggregation pheromone of the German cockroach. *Bioorg. Med. Chem.* 1996, 4, 401-408). Major diastereomer (5α,6α-epoxide): $^1$H NMR (400 MHz, CDCl$_3$) δ 5.56 (dt, J=3.3, 1.6 Hz, 1H), 4.95 (tt, J=11.3, 4.9 Hz, 1H), 2.93 (d, J=4.5 Hz, 1H), 2.30-2.05 (m, 3H), 2.07-1.87 (m, 5H), 1.78-1.17 (m, 9H), 1.11 (s, 2H), 1.04 (s, 1H), 0.94 (m, 3H); $^{13}$C NMR (101 MHz, CDCl$_3$) δ 170.2, 159.0, 114.2, 71.14, 65.3, 58.5, 54.1, 44.7, 42.6, 36.0, 35.3, 32.3, 31.9, 28.4, 28.0, 27.4, 27.1, 21.3 (overlapping peaks), 19.9, 15.8, 15.0; this compound did not ionize by ESI-MS. Minor diastereomer: 4.77 (tt, J=11.3, 4.9 Hz, 1H), 3.12, (d, J=4.5 Hz, 1H).

3β-Acetoxy-5α,6α-epoxy-17-(3-pyridyl)-Δ16-androst-16-ene (7) and isomer

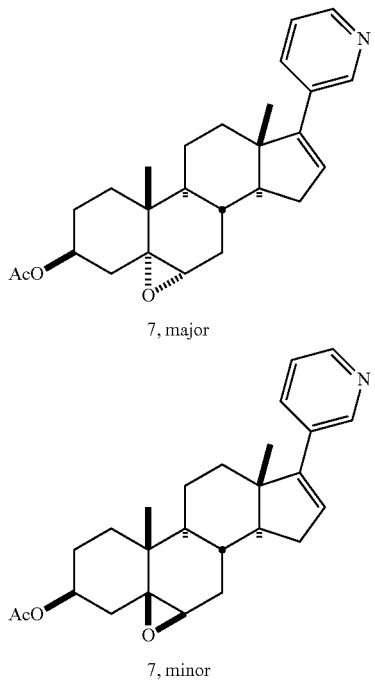

Compound 6 (1.9 g, 3.97 mmol) was coupled as described for the reaction of 3 to 4 except that the temperature was reduced to 50° C. The organic extract was purified by automatic purification to isolate 1.4 g of a pale yellow oil (82%). The isomeric ratio of 7:3 (7, major:7, minor) was maintained from the previous step. Major isomer: $^1$H NMR (400 MHz, CDCl$_3$) δ 8.59 (s, 1H), 8.53-8.37 (m, 1H), 7.62 (d, J=9.3 Hz, 1H), 7.25-7.14 (m, 1H), 5.97 (s, 1H), 5.01-4.89 (m, 1H), 2.94 (d, J=4.4 Hz, 1H), 2.10-1.91 (m, 7H), 1.90-1.19 (m, 13H), 1.09 (m, 3H), 0.98 (m, 3H). $^{13}$C NMR (101

MHz, CDCl$_3$) δ 170.3, 147.7, 134.0, 132.1, 129.2, 128.7, 128.5, 123.2, 71.4, 65.4, 59.0, 57.4, 47.4, 42.6, 36.2, 35.32, 35.29, 34.9, 32.1, 31.6, 28.5, 28.4, 27.3, 21.4, 20.6, 16.5, 16.0. Minor isomer: 4.81-4.89 (m, 1H), 3.13 (d, J=2.4 Hz, 1H).

3β-Hydroxy-5,6α-epoxy-17-(3-pyridyl)-Δ16-androstane (8)

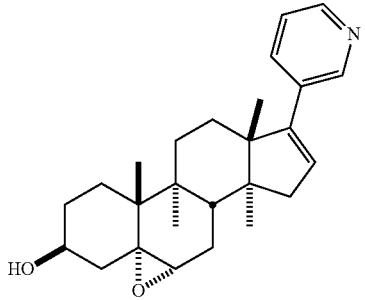

Compound 7 was deacylated as for 5. The crude mixture was purified by silica column to isolated 21.3 mg of a white powder (81%). IR (neat) 3329, 1687, 1439, 1378.3 1250 cm$^{-1}$; $^1$H NMR (400 MHz, CDCl$_3$) δ 8.62 (s, 1H), 8.49 (s, 1H), 7.95 (d, J=7.6, 1H), 7.50 (t, J=6.4, 1H), 6.13 (s, 1H), 3.84 (s, 1H), 3.63 (d, J=6.0, 1H), 3.38 (s, 1H), 3.04-2.86 (m, 1H), 2.30 (d, J=15.9 Hz, 2H), 1.55 (m, 7H), 1.40 (m, 9H), 1.11 (m, 3H), 0.98 (s, 3H), 0.71 (s, 1H); $^{13}$C NMR (101 MHz, CDCl$_3$) δ 151.5, 147.8, 133.7, 133.7, 132.9, 129.1, 123.0, 69.3, 68.6, 65.9, 63.6, 63.1, 59.0, 57.4, 57.2, 47.3, 42.6, 39.4, 42.2, 39.8, 37.3, 35.1, 34.9, 32.3, 31.6, 31.1, 28.5, 28.4, 20.6, 21.7, 16.5, 16.0; HRMS calculated for C$_{24}$H$_{32}$NO$_2$ (M$^+$+1): 366.2433. found 366.2430.

3β-Acetoxy-androst-17-one, ethylene ketal

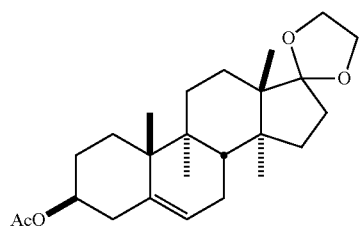

Compound 2 (2.0 g, 6.03 mmol) in a dry microwave vial was dissolved in triethyl orthoformate (2.4 mL) and ethylene glycol (1.6 mL) to a concentration of 1.5 M. Toluenesulfonic acid (57 mg, 0.30 mmol) was added, and the reaction vessel was capped. The reaction was heated to 90° C. for 20 min in the microwave. The mixture was diluted with methylene chloride and washed with saturated sodium bicarbonate, water, and brine. The mixture was dried over NaSO$_4$ and purified by silica flash columntography (20 g silica, 20% EtOAc/hexanes) to yield 2.02 g of the title compound as a white solid (90%). The analytical data matched reported values.

3β-Acetoxy-5α,6α-epoxy-androst-17-one, ethylene ketal (9) and minor isomer

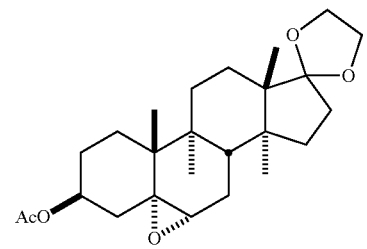

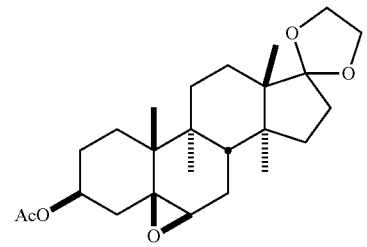

The above ketal (2.02 g, 5.44 mmol) was dissolved in methylene chloride (50 mL, 0.1 M) and cooled to 0° C. Chloroperoxybenzoic acid (77% pure, 1.82 g, 8.16 mmol) was added and the mixture stirred overnight, warming to rt. Saturated aqueous sodium bicarbonate (50 mL) was added, and the mixture stirred for 1 h at rt. The mixture was extracted twice more with methylene chloride, washed with brine, and dried over NaSO$_4$. The crude material was purified by automatic purification system (40 g silica, 10% to 20% ethyl acetate/hexanes) to obtain 1.77 g (84%) of a white solid, in a ca. 10:1 mixture of the α:β epoxides. Major isomer: $^1$H NMR (400 MHz, CDCl$_3$) δ 4.99-4.88 (m, 1H), 3.98-3.72 (m, 4H), 2.88 (d, J=4.4 Hz, 1H), 2.15 (s, 1H), 2.00 (s, 3H), 1.98-1.84 (m, 3H), 1.81-1.74 (m, 1H), 1.71 (dd, J=6.7, 3.0 Hz, 1H), 1.67 (m, 1H), 1.57-1.48 (m, 2H), 1.43 (s, 3H), 1.33 (s, 5H), 1.25 (s, 1H), 1.21-1.13 (m, 1H), 1.07 (s, 3H), 0.78 (s, 3H). Minor isomer: 4.81-4.71 (m, 1H), 3.08 (d, J=2.0 Hz, 1H).

3β-Acetoxy-5,6-seco-5-keto-17-triflyl-Δ16-androstan-6-al (17)

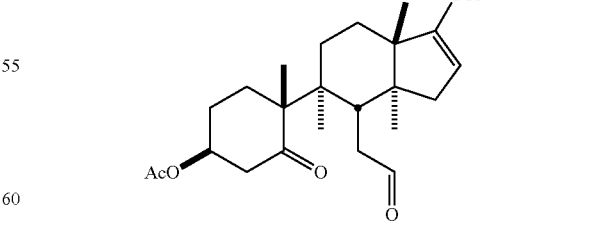

Compound 3 (2.50 g, 5.35 mmol) was dissolved in methylene chloride (220 mL), methanol (25 mL), and pyridine (13 mL; final concentration 0.02 M) and cooled to −78° C. Ozone was bubbled through a 0.5 μm aquarium diffuser stone for 4.5 minutes at a flow rate of 6 psi. This exposure level was found to be optimal in sparing the over-reaction of the vinyl triflate. Once ozone addition was done, the mixture was rapidly and vigorously sparged with N₂. Dimethylsulfide (2.5 mL, 42.8 mmol) was added at −78° C., and the mixture stirred for 30 min at this temperature. The mixture was allowed warmed to rt over the course of 1 h. Water was added and the organic layer was separated, washed with brine, and dried over NaSO₄. The mixture was concentrated onto silica gel in vacuo, careful to keep the temperature at or below rt to avoid product decomposition, and purified by automatic purification (40 g silica, 10% to 20% to 50% EtOAc/hexanes) to yield 1.39 g of 17 as a clear oil (53%). IR (neat) 1735, 1725, 1703, 1418, 1377 cm⁻¹; ¹H NMR (400 MHz, CDCl₃) δ 9.65 (s, 1H), 5.57 (t, J=1.3, Hz, 1H), 5.39 (m, 1H), 3.03 (dd, J=14.4, 4.4 Hz, 1H), 2.60-2.20 (m, 4H), 2.19-2.05 (m, 2H), 2.04 (s, 3H), 2.02-1.73 (m, 6H), 1.75-1.55 (m, 3H), 1.55-1.39 (m, 1H), 1.08 (s, 3H), 1.02 (s, 3H); ¹³C NMR (101 MHz, CDCl₃) δ 215.4, 201.5, 170.1, 158.3, 114.2, 73.1, 52.3, 44.7, 43.3, 43.2, 42.2, 34.0, 32.8, 32.4, 29.5, 25.2, 22.4, 21.2, 17.7, 14.7, one overlapping peak; this product did not ionize by ESI-MS.

3β-Acetoxy-5-keto-5,6-seco-17-pyridyl-androst-16-en-6-al

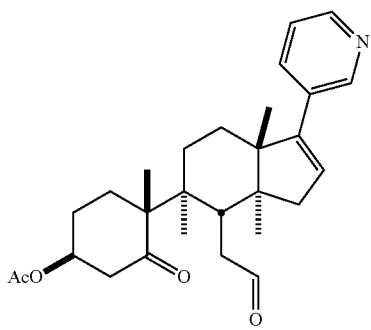 [SMILES: CC(=O)O[C@H]1CC[C@](C)([C@@]2(C)CC[C@]3(C)C(c4cccnc4)=CC[C@@]3(C)[C@@H]2CC=O)C(=O)C1]

Compound 17 (400 mg, 0.81 mmol) was coupled as described for 4, however the temperature was reduced to 50° C. Automatic purification (4 g silica, 25% to 60% EtOAc/hexanes) afforded 290 mg of the title compound as a clear oil (85%). ¹H NMR (400 MHz, CDCl₃) δ 9.61 (s, 1H), 8.52 (s, 1H), 8.40 (d, J=4.9 Hz, 1H), 7.53-7.44 (m, 1H), 7.16 (dd, J=7.9, 4.8 Hz, 1H), 5.87 (dd, J=3.0, 1.9 Hz, 1H), 5.31 (t, J=2.9 Hz, 1H), 2.98 (dd, J=14.4, 4.4 Hz, 1H), 2.42 (dd, J=6.1, 1.8 Hz, 1H), 2.35 (m, 1H), 2.28-2.17 (m, 1H), 2.13 (m, 1H), 2.05-1.99 (m, 2H), 1.97 (s, 3H), 1.95 (m, 4H), 1.85-1.70 (m, 3H), 1.60-1.47 (m, 3H), 1.02 (s, 3H), 0.98 (s, 3H); ¹³C NMR (101 MHz, CDCl₃) δ 215.8, 202.1, 170.1, 151.2, 148.1, 147.7, 133.7, 132.0, 128.4, 123.1, 73.2, 55.5, 52.4, 47.3, 44.3, 43.2, 42.3, 35.3, 34.1, 33.0, 32.7, 25.2, 22.9, 21.2, 21.04, 17.7, 16.1; MS calculated for C₂₆H₃₃NO₄ (M⁺+H): 424.249. found 424.294.

3β-Acetoxy-6a-aza-6a-homo-17-pyridyl-androst-16-ene (18)

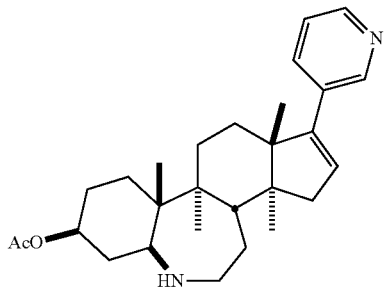

3β-Acetoxy-5-keto-5,6-seco-17-pyridyl-androst-16-en-6-al (290 mg, 0.684 mmol) was dissolved in dry methanol (11.5 mL, 0.05 M) and cooled to 0° C. Ammonia (0.16 mL of a 7.0 M methanolic solution, 1.09 mmol) was added, followed by triethylamine (0.170 mL, 1.46 mmol). The solution was stirred for 10 min at 0° C., then sodium cyanoborohydride (107 mg, 1.71 mmol) was added in one portion. The mixture was allowed to slowly rise to rt and was stirred for 30 h, at which point MS indicated completion. The solvent was removed, and 10 mL of aqueous 2.0 N HCl was added. Organic byproducts were extracted away in methylene chloride, then the aqueous phase was basified to pH 13 using 5 mL of aqueous 4.0 N NaOH. The product was extracted with methylene chloride. This organic layer was washed with brine and dried over NaSO₄. Concentration of this layer yielded 247 mg of a white foam (88%) that was used directly in the next step. ¹H NMR (400 MHz, CDCl₃) δ 8.56 (s, 1H), 8.42 (d, J=5.7, 1H), 7.64 (d, J=8.1, 1H), 7.25 (dd, J=8.0, 4.8 Hz, 1H), 5.98 (m, 1H), 5.28 (s, 1H), 3.42-3.21 (m, 2H), 2.39-2.22 (m, 1H), 2.00 (m, 5H), 1.93-1.57 (m, 7H), 1.57-1.38 (m, 3H), 1.34 (m, 3H), 1.30-1.17 (m, 2H), 1.14-0.94 (m, 8H); ¹³C NMR (101 MHz, CDCl₃) δ 170.5, 151.3, 147.3, 134.1, 132.9, 132.9, 128.8, 123.4, 70.5, 62.5, 57.4, 56.4, 53.6, 46.8 44.4, 40.3, 39.9, 36.0, 35.1, 32.9, 28.5, 24.7, 21.3, 21.0, 16.5, 13.9, 8.9; MS calculated for C₂₆H₃₇N₂O₂ (M⁺+H): 409.285. found 409.140.

6a-Aza-6a-homo-17-pyridyl-androst-16-en-3β-ol (19)

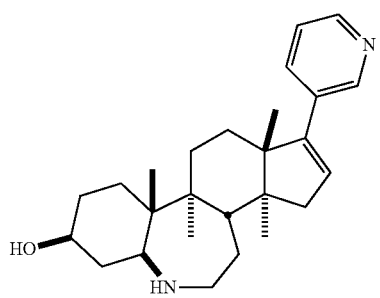

Compound 18 was deacylated as described for 5. The mixture was purified by flash chromatography (200 mg silica, 5 to 10% MeOH/CH₂Cl₂) to isolate 67.1 mg of 19 as a white solid (47%). IR (neat) 3306, 1456, 1411; ¹H NMR (400 MHz, CDCl$_3$) δ 8.69-8.56 (d, J=1.6 Hz, 1H), 8.46 (dt, J=4.9, 1.6 Hz, 1H), 7.65 (dt, J=7.8, 1.8 Hz, 1H), 7.23 (m, 1H), 6.08-5.94 (m, 1H), 3.65-3.57 (m, 1H), 3.23-3.09 (m, 1H), 2.97 (td, J=12.0, 5.8 Hz, 1H), 2.66 (dd, J=11.9, 4.3 Hz, 1H), 2.38 (m, 1H), 2.17-2.03 (m, 1H), 2.05-1.90 (m, 3H), 1.90-1.78 (m, 3H), 1.70 (m, 3H), 1.64-1.36 (m, 4H), 1.34-1.17 (m, 2H), 1.05 (s, 3H), 0.96 (ds, 3H); $^{13}$C NMR (101 MHz, CDCl$_3$) δ 151.8, 147.8, 147.8, 133.7, 132.9, 128.6, 123.1, 60.5, 58.04, 56.8, 46.9, 45.2, 41.4, 39.2, 35.4, 35.3, 33.3, 32.3, 31.4, 25.8, 22.4, 21.6, 16.5, 14.0; HRMS calculated for C$_{24}$H$_{35}$N$_2$O (M$^+$+H): 367.2749. found 367.2740.

6a-Acyl-6a-aza-6a-homo-17-pyridyl-androst-16-en-3β-ol (21)

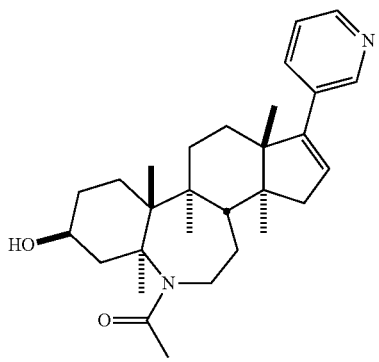

Compound 18 (30 mg, 0.074 mmol) was dissolved in methylene chloride (0.75 mL, 0.1 M). Triethylamine (15.5 μL, 0.111 mmol) was added, followed by acetic anhydride (8.4 μL, 0.088 mmol). The mixture was stirred for 2 h, then diluted with water and methylene chloride. The was extracted with additional methylene chloride, washed with brine, and dried over NaSO$_4$. The crude material was purified to obtain 15 mg of a white solid. This was deacylated as for 5 to obtain a residue, that was purified by preparative HPLC to yield 1.2 mg of a white solid (4%). IR (neat) 3370, 1696, 1447, 1383 cm$^{-1}$; $^1$H NMR (500 MHz, CDCl$_3$) δ 8.63 (s, 1H), 8.49 (s, 1H), 7.74 (d, J=8.3 Hz, 1H), 7.31 (m, 1H), 6.03 (dd, J=3.5, 1.8 Hz, 1H), 3.59-3.47 (m, 1H), 3.37 (m, 1H), 2.31 (m, 1H), 2.13 (s, 3H), 2.07-1.87 (m, 6H), 1.85-1.75 (m, 4H), 1.65-1.58 (m, 3H), 1.52-1.40 (m, 3H), 1.30 (s, 1H), 1.24 (s, 3H), 1.04 (s, 3H); $^{13}$C NMR (126 MHz, CDCl$_3$) δ 169.8, 151.0, 146.6, 146.5, 134.8, 131.4, 129.5, 123.6, 70.0, 69.6, 63.7, 57.9, 57.8, 46.8, 41.0, 38.1, 36.3, 35.4, 34.2, 32.6, 31.1, 30.8, 24.1, 23.9, 16.5, 16.0; HRMS calculated for C$_{26}$H$_{36}$N$_2$O$_2$ (M$^+$+H): 409.2875. found 409.2827.

3β-Acetoxy-17-triflyl-androst-16-en-6-ol

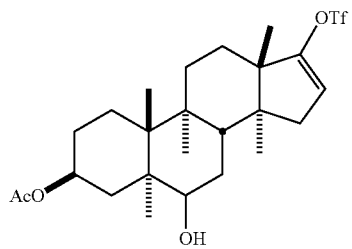

Compound 3 (2.1 g, 4.54 mmol) was added to a dry flask, placed under inert atmosphere, and dissolved in dry tetrahydrofuran (23 mL, 0.2 M). This solution was cooled to −10° C. and a fresh bottle of borane (1.0 M in THF, 4.77 mmol) was added evenly over the course of 1 h at −10° C. The solution was allowed to slowly rise to rt and stir over the course of 8 h. The mixture was brought to 0° C., and water (23 mL) was very slowly added until the excess borane was quenched. Sodium perborate (768 mg, 4.99 mmol) was added in one portion, and the mixture allowed to warm to rt and stir overnight. Salt was added to facilitate separation of the phases, and the mixture was extracted twice more with tetrahydrofuran. The solution was rigorously dried with MgSO$_4$ and purified using an automatic purification system (40 g silica, 10% to 35% EtOAc/hexanes) to obtain 1.59 g of the title compound as a clear oil (76%). $^1$H NMR (400 MHz, CDCl$_3$) δ 5.57 (dd, J=3.4, 1.7 Hz, 1H), 4.68 (tt, J=11.4, 4.9 Hz, 1H), 3.44 (td, J=10.7, 4.5 Hz, 1H), 2.33-2.13 (m, 2H), 2.11-1.96 (m, 3H), 1.87 (s, 1H), 1.81-1.57 (m, 6H), 1.57-1.39 (m, 3H), 1.39-1.17 (m, 4H), 1.17-1.05 (m, 2H), 0.96 (s, 3H), 0.87 (s, 3H); $^{13}$C NMR (101 MHz, CDCl$_3$) δ 170.6, 159.1, 114.4, 73.3, 69.1, 54.1, 53.9, 51.9, 44.9, 40.4, 36.7, 36.5, 32.5, 32.3, 28.5, 28.3, 27.1, 21.4, 20.4, 15.3, 13.3 (one carbon peak likely overlapping); this compound did not ionized by ESI-MS.

3β-Acetoxy-17-triflyl-androst-16-en-6-one (27)

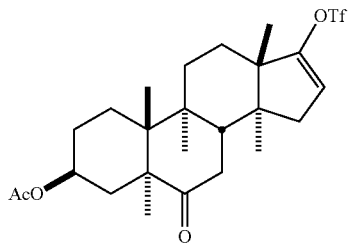

3β-Acetoxy-17-triflyl-androst-16-en-6-ol (0.935 g, 1.95 mmol) was dissolved in dry dichloromethane (65 mL, 0.03 M). Magnesium sulfate (589 mg, 4.88 mmol) was added, followed by N-methyl morpholine (503 mg, 4.29 mmol). The solution was cooled to 0° C., and tetrapropylammonium perruthenate (68.4 mg, 0.195 mmol) was added. The reaction was allowed to slowly warm to rt over the course of 1 h, then the mixture was adsorbed directly onto silica gel and purified via automated purification system (24 g, 10% to 25% EtOAc/hexanes) to obtain 729 mg of 27 as a white solid (78%). IR (neat) 1731, 1715, 1420, 1377 cm$^{-1}$; $^1$H NMR (400 MHz, CDCl$_3$) δ 5.59 (dd, J=3.4, 1.7 Hz, 1H), 4.67 (tt, J=11.6, 4.8 Hz, 1H), 2.32 (m, 2H), 2.20 (m, 1H), 2.06 (s, 1H), 2.04 (s, 3H), 1.99-1.92 (m, 2H), 1.92-1.71 (m, 5H), 1.71-1.12 (m, 7H), 0.97 (s, 3H), 0.81 (s, 3H); $^{13}$C NMR (101 MHz, CDCl$_3$) δ 209.1, 170.6, 158.7, 114.4, 72.6, 56.8, 54.2, 54.1, 45.3, 45.2, 41.0, 36.1, 35.8, 32.3, 28.4, 26.8, 26.1, 21.3, 20.8, 15.2, 13.1; this compound did not ionize by ESI-MS.

3β-Acetoxy-17-triflyl-androst-16-en-6-one (28)

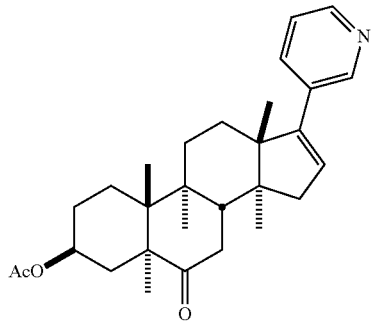

Compound 27 (403 mg, 0.843 mmol) was coupled as described for 4. This was purified by automatic purification systems (4 g silica, 20% to 50% EtOAc/hexanes) to obtain 263 mg of 27 as a white powder (77%). IR (neat) 1730, 1710, 1444, 1371 cm$^{-1}$; $^1$H NMR (400 MHz, CDCl$_3$) δ 8.61 (dd, J=2.4, 0.9 Hz, 1H), 8.47 (dd, J=4.8, 1.7 Hz, 1H), 7.64 (ddd, J=7.9, 2.3, 1.7 Hz, 1H), 7.23 (ddd, J=7.9, 4.8, 0.9 Hz, 1H), 5.98 (dd, J=3.3, 1.8 Hz, 1H), 4.68 (m, 1H), 2.49-2.35 (m, 1H), 2.31 (dd, J=12.6, 3.0 Hz, 1H), 2.25-2.15 (m, 1H), 2.15-2.05 (m, 4H), 2.03 (s, 3H), 1.99-1.91 (m, 1H), 1.81 (m, 4H), 1.68-1.46 (m, 4H), 1.46-1.13 (m, 2H), 1.01 (s, 3H), 0.83 (s, 3H); $^{13}$C NMR (101 MHz, CDCl$_3$) δ 209.8, 170.6, 151.4, 148.0, 147.8, 133.8, 132.6, 128.9, 123.1, 72.7, 57.4, 56.7, 54.0, 47.8, 46.4, 41.0, 36.4, 36.2, 34.9, 31.5, 26.8, 26.1, 21.3, 16.6, 13.1; MS calculated for C$_{26}$H$_{33}$NO$_3$ (M$^+$+H): 408.254. found 408.052.

3β-Hydroxy-17-(3-pyridyl)-androst-16-en-6-one (29)

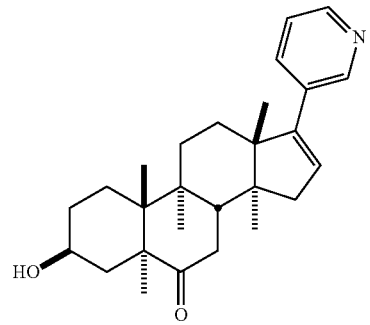

Compound 28 (30 mg, 0.074 mmol) was deacylated as for 5. 25 mg of a white solid was isolated (92%), then further subjected to preparative HPLC purification to obtain 10.5 mg of a white solid. IR (neat) 3335, 1705, 1415, 1385 cm$^{-1}$; $^1$H NMR (500 MHz, CDCl$_3$) δ 8.62 (d, J=2.3 Hz, 1H), 8.48 (dd, J=4.9, 1.6 Hz, 1H), 7.65 (dt, J=7.9, 2.0 Hz, 1H), 7.24 (ddd, J=8.0, 4.9, 0.9 Hz, 1H), 5.99 (dd, J=3.3, 1.8 Hz, 1H), 3.60 (tt, J=11.2, 4.6 Hz, 1H), 2.48-2.32 (m, 1H), 2.32-2.18 (m, 2H), 2.09 (m, 3H), 1.94 (m, 1H), 1.92-1.85 (m, 1H), 1.85-1.76 (m, 3H), 1.61-1.48 (m, 2H), 1.48-1.36 (m, 2H), 1.29 (m, 1H), 1.02 (s, 3H), 0.83 (s, 3H); $^{13}$C NMR (126 MHz, CDCl$_3$) δ 210.4, 151.5, 148.1, 147.9, 133.7, 132.6, 128.9, 123.1, 70.6, 57.5, 57.0, 54.1, 47.8, 46.4, 41.1, 36.5, 36.4, 34.9, 31.5, 30.7, 30.1, 21.5, 16.6, 13.2; HRMS calculated for C$_{24}$H$_{32}$NO$_2$ (M$^+$+H): 366.2433. found 366.2454.

6a-Aza-6a-homo-7-keto-17-(3-pyridyl)-androst-16-en-3β-ol (30)

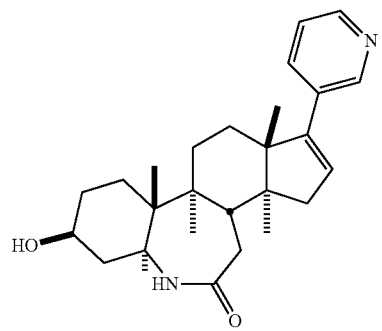

CAUTION! This reaction generates hydrazoic acid, a known explosion hazard. Appropriate safety precautions should be observed. Compound 29 (51 mg, 0.125 mmol) was dissolved in acetic acid (glacial, 2.1 mL, 0.06 M). Sodium azide (13.4 mg, 0.26 mmol) was added, followed by methanesulfonic acid (81 μL, 0.125 mmol). The mixture was stirred for 5 h, then quenched with aqueous saturated sodium bicarbonate until the pH was neutral. The mixture was extracted with chloroform, washed with brine, and dried over NaSO$_4$. The crude material (52 mg) was isolated and used without further purification. 21 mg was deacylated as described for 5 and purified by preparative HPLC to obtain 7.7 mg of a pale yellow solid (41%). IR (neat) 3286, 1648, 1444, 1388 cm$^{-1}$; $^1$H NMR (400 MHz, CDCl$_3$) δ 8.62 (dd, J=2.3, 0.9 Hz, 1H), 8.49 (dd, J=4.8, 1.6 Hz, 1H), 7.65 (dt, J=8.0, 1.9 Hz, 1H), 7.25 (ddd, J=7.9, 4.8, 0.9 Hz, 1H), 6.00 (dd, J=3.4, 1.8 Hz, 1H), 5.39 (d, J=5.5 Hz, 1H), 3.65 (tt, J=11.2, 4.3 Hz, 1H), 3.52-3.32 (m, 1H), 2.46-2.31 (m, 3H), 2.23 (m, 1H), 2.15-1.92 (m, 5H), 1.90 (m, 2H), 1.71 (m, 1H), 1.64-1.25 (m, 4H), 1.21-1.08 (m, 2H), 1.05 (s, 3H), 0.94 (s, 3H); $^{13}$C NMR (101 MHz, CDCl$_3$) δ 175.8, 151.5, 148.0, 147.8, 133.7, 132.6, 128.5, 123.1, 68.7, 59.0, 57.1, 56.7, 47.1, 40.6, 38.9, 38.7, 35.6, 35.4, 33.1, 32.9, 30.9, 22.8, 16.4, 12.4; HRMS calculated for C$_{24}$H$_{32}$N$_2$O$_2$ (M$^+$+H): 381.2542. found 381.2548.

6a-Aza-6a-homo-6a,6-tetrazolo-17-(3-pyridyl)-androst-16-en-3β-ol (31)

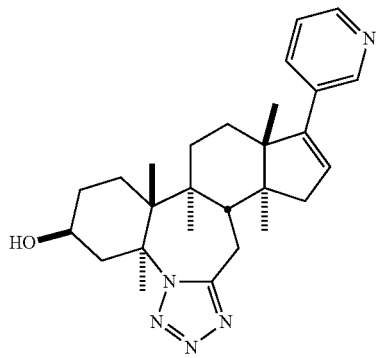

31

Compound 27 (51 mg, 0.125 mmol) was dissolved in hexafluoroisopropanol (0.3 mL, 0.4 M). Azidotrimethylsilane (41 µL, 0.250 mmol) was added, followed by triflic acid (14 µL, 0.154 mmol) and the mixture was stirred at rt overnight. The solution was neutralized with sodium bicarbonate and extracted with chloroform. The organic layers were washed with brine, dried over NaSO$_4$, and purified by silica flash chromatography (200 mg silica, 1 to 5% MeOH/CH$_2$Cl$_2$) to obtain 25 mg (45%) as a pale yellow solid. This was deacylated as for 5 and purified by preparative TLC (75% EtOAc/hexanes eluent) to obtain 11 mg of a white solid (49%). IR (neat) 3264, 1586, 1566, 1536, 1433, 1390 cm$^{-1}$; $^1$H NMR (400 MHz, CDCl$_3$) δ 8.21 (dd, J=2.3, 0.9 Hz, 1H), 8.09 (dd, J=4.9, 1.6 Hz, 1H), 7.52-7.40 (m, 1H), 7.04 (ddd, J=8.0, 4.9, 0.9 Hz, 1H), 5.78 (dd, J=3.4, 1.7 Hz, 1H), 4.16 (dd, J=10.8, 6.1 Hz, 1H), 3.46-3.27 (m, 1H), 3.10 (m, 1H), 2.48-2.31 (m, 1H), 2.30-2.13 (m, 3H), 1.97 (m, 1H), 1.87-1.67 (m, 3H), 1.61 (m, 2H), 1.45 (m, 1H), 1.35-0.90 (m, 5H), 0.71 (s, 3H), 0.31 (s, 3H); $^{13}$C NMR (101 MHz, CDCl$_3$) δ 159.3, 154.9, 151.0, 150.7, 138.6, 136.9, 132.7, 127.6, 71.9, 67.8, 62.2, 60.1, 50.7, 42.7, 39.7, 40.0, 39.4, 38.1, 36.7, 34.3, 31.0, 26.9, 19.9, 15.2; HRMS calculated for C$_{24}$H$_{36}$N$_5$O (M$^+$+H): 406.2607. found 406.2578.

6α-Methylamine-17-(3-pyridyl)-androst-16-en-3β-ol (32)

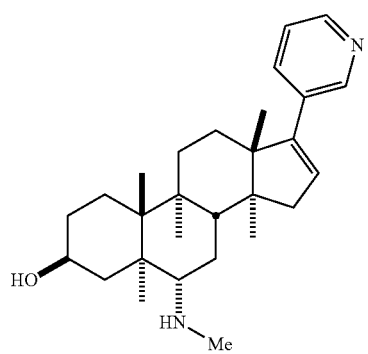

32

Compound 27 (50 mg, 0.123 mmol) was dissolved in ethanol (1.2 mL, 0.1 M) and cooled to 0° C. Methylamine (14.4 µL of a 33% w/v solution in ethanol, 0.153 mmol) was added and stirred for 5 min. Sodium cyanoborohydride (12 mg, 0.185 mmol) was added in one portion, and the reaction allowed to stir for 24 h, warming to rt. This was diluted with methanol (4.0 mL, to 0.03 M), and potassium carbonate (136 mg, 0.984 mmol) was added to deacylate the C3-hydroxyl. After stirring an additional 20 h, the solution was processed as for 6. Preparative HPLC purification furnished 3.5 mg as a white solid (7%). IR (neat) 3319, 1589, 1418, 1380 cm$^{-1}$; $^1$H NMR (500 MHz, CDCl$_3$) δ 8.54-8.49 (m, 1H), 8.48-8.44 (m, 1H), 7.57 (ddt, J=22.1, 7.9, 2.0 Hz, 1H), 7.13 (ddd, J=8.0, 4.9, 0.9 Hz, 1H), 5.88 (dd, J=3.3, 1.8 Hz, 1H), 3.57 (s, 1H), 2.78-2.61 (dt, J=14.0, 5.5 Hz, 1H), 2.19-2.13 (m, 1H), 2.11-1.74 (m, 7H), 1.74-1.45 (m, 6H), 1.45-1.22 (m, 5H), 1.21-1.01 (m, 2H), 0.99-0.90 (m, 3H), 0.71 (s, 3H); $^{13}$C NMR (126 MHz, CDCl$_3$) δ 151.6, 149.9, 149.2, 136.6, 133.7, 129.0, 123.0, 71.0, 70.0, 62.0, 59.5, 57.0, 54.5, 47.7, 46.7, 45.0, 43.4, 42.7, 31.3, 28.9, 27.3, 20.9, 16.9, 16.1, 15.2; HRMS calculated for C$_{25}$H$_{36}$N$_2$O (M$^+$+H): 381.2906. found 381.2867.

Assignment of the stereochemistry of the 6-methylamine group was based of similar compounds described in Beuchet et al., *Bioorg. Med. Chem. Lett.* 1998, 8, 3627, illustrated below in Scheme 2.

Scheme 2.

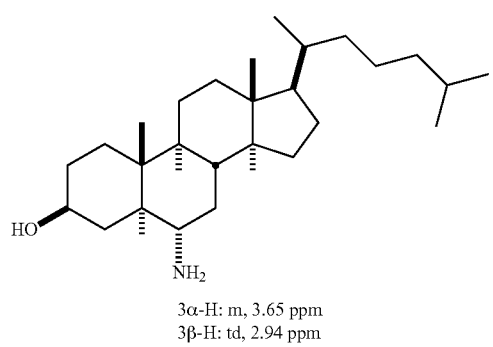

3α-H: m, 3.65 ppm
3β-H: td, 2.94 ppm

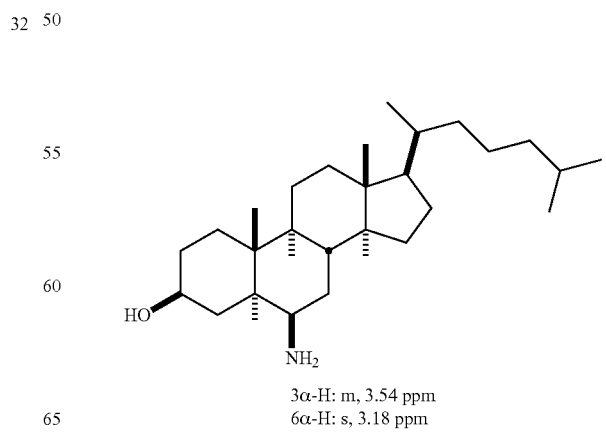

3α-H: m, 3.54 ppm
6α-H: s, 3.18 ppm

6-Oxime-17-(3-pyridyl)-androst-16-en-3β-ol (33)

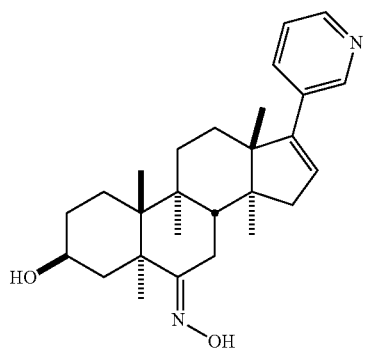

Compound 28 (50 mg, 0.114 mmol) was added to a flask along with sodium acetate (66 mg, 0.800 mmol) and hydroxylamine hydrochloride (56 mg, 0.800 mmol). Ethanol (3.8 mL, 0.03 M) was added, followed by two drops of water. The solution was stirred at rt overnight, then concentrated under a stream of $N_2$. The mixture was dissolved in chloroform, washed with water and brine, and dried over $NaSO_4$ to obtain 43 mg of a white solid (84%). This was further purified by preparative HPLC to obtain 7.8 mg of a white solid. IR (neat) 3270, 1730.2, 1651, 1441, 1376 cm$^{-1}$; $^1$H NMR (400 MHz, CDCl$_3$) δ 8.59 (d, J=2.1 Hz, 1H), 8.54-8.38 (m, 1H), 7.88 (dt, J=8.0, 1.9 Hz, 1H), 7.51-7.35 (m, 1H), 6.14 (dd, J=3.4, 1.8 Hz, 1H), 3.65-3.54 (m, 1H), 2.40 (m, 1H), 2.23 (m, 1H), 2.18-2.05 (m, 2H), 2.00 (dq, J=13.3, 2.5 Hz, 1H), 1.96-175 (m, 5H), 1.54 (s, 3H), 1.51-1.32 (m, 3H), 1.32-1.15 (m, 2H), 1.11 (s, 3H), 0.88 (s, 3H). $^{13}$C NMR (101 MHz, CDCl$_3$) δ 162.9, 155.1, 150.4, 138.8, 137.5, 133.6, 127.6, 100.0, 74.4, 61.4, 58.5, 53.6, 42.7, 39.9, 38.9, 38.2, 35.3, 34.9, 34.2, 33.1, 32.0, 25.2, 20.0, 15.9; HRMS calculated for $C_{24}H_{32}N_2O_2$ (M$^+$+H): 381.2542. found 381.2522.

3β-Acetoxy-6-cyano-6-hydroxy-17-(3-pyridyl)-androst-16-ene (mixture of C6 isomers) (34)

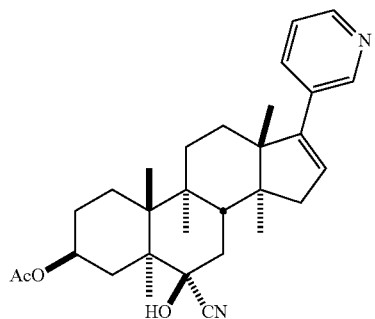

Compound 27 (220 mg, 0.540 mmol) was added to a microwave vial and dissolved in ethanol (1.5 mL, 0.5 M). To this was added potassium cyanide (620 mg, 9.52 mmol) and acetic acid (0.674 mL, 13.3 mmol) and the vial was quickly capped. The vial was heated to 90° C. for 20 min in the microwave reactor. The solid material was removed by filtration, and the filtrate adsorbed directly onto silica gel as an acidic solution. This was purified by automatic purification system (4 g, 1% MeOH/DCM) to obtain 210 mg of a white solid (66%). IR (neat): 3175, 2211, 1727 cm$^{-1}$; $^1$H NMR (400 MHz, CDCl$_3$) δ 8.61 (dd, J=2.3, 0.9 Hz, 1H), 8.48 (dd, J=4.9, 1.6 Hz, 1H), 7.69 (dt, J=7.9, 1.9 Hz, 1H), 7.28 (dd, J=4.8, 0.9 Hz, 1H), 6.01 (dd, J=3.3, 1.8 Hz, 1H), 4.74 (tt, J=11.1, 5.0 Hz, 1H), 2.41 (m, 2H), 2.27 (m, 1H), 2.17 (m, 1H), 2.07 (s, 3H), 2.04-1.85 (m, 2H), 1.85-1.62 (m, 4H), 1.62-1.35 (m, 5H), 1.16 (s, 3H), 1.06 (s, 3H), 0.91 (s, 1H); $^{13}$C NMR (101 MHz, CDCl$_3$) δ 170.7, 151.3, 147.3, 134.2, 133.0, 129.1, 123.4, 121.8, 72.8, 68.7, 56.3, 53.7, 52.5, 47.5, 45.0, 38.1, 36.6, 35.0, 31.67, 31.62, 26.88, 26.84, 21.4, 20.8, 16.8, 14.2; MS calculated for (M$^+$+H): 435.265. found 435.212.

3β-Acetoxy-6-cyano-17-(3-pyridyl)-androst-6,16-diene (35, minor product) and 3β-acetoxy-6-cyano-17-(3-pyridyl)-androst-5,16-diene (36, major product)

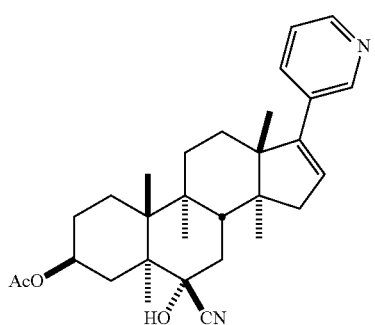

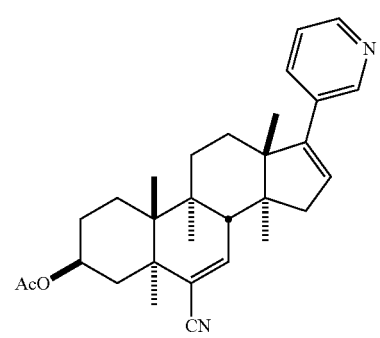

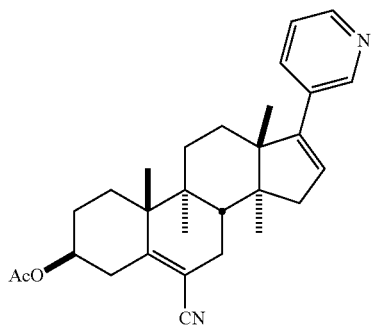

36

The mixture of compounds 34 (210 mg, 0.484 mmol) was added to a microwave vial and dissolved in pyridine (0.48 mL, 1.0 M). Fresh phosphorus oxychloride (90 μL, 0.967 mmol) was added and was heated to 115° C. for 1 h. The solution was cooled, and quenched with cold aqueous 1.0 N HCl (2.5 mL). This was basified with 3.5 mL of aqueous saturated sodium bicarbonate and extracted with chloroform. The pooled organic layers were washed with brine and dried over NaSO$_4$, then purified by automatic purification system (4 g silica, 0% to 2% MeOH/DCM) to obtain 113 mg of a mixture of 35 and 36 as a pale yellow foam (56%). The mixture was determined to be ca. 1:5 (35:36) by $^1$H-NMR analysis.

For the mixture: IR (neat) 2212, 1733, 1439, 1371 cm$^{-1}$; $^1$H NMR (400 MHz, CDCl$_3$) δ 8.54 (s, 1H), 8.41 (s, 1H), 7.57 (d, J=7.9 Hz, 1H), 7.17 (dd, J=7.9, 4.5 Hz, 1H), 6.05-5.84 (m, 1H), 4.71, 4.61 (tt, J=11.8, 4.6 Hz, 1H), 2.45-2.18 (m, 3H), 2.18-2.04 (m, 2H), 2.03-1.96 (m, 3H), 1.96-1.83 (m, 2H), 1.83-1.69 (m, 2H), 1.69-1.29 (m, 7H), 1.27-1.14 (m, 1H), 1.08 (s, 3H), 1.05-0.85 (m, 3H), 0.79 (s, 1H); $^{13}$C NMR (101 MHz, CDCl$_3$) δ 170.1, 157.7, 151.3, 148.2, 147.9, 147.3, 133.8, 129.0, 123.2, 118.6, 107.3, 72.0, 56.7, 49.0, 47.2, 38.4, 36.2, 36.0, 34.9, 33.5, 31.6, 29.7, 27.2, 21.3, 20.6, 19.6, 16.5; MS calculated for C$_{27}$H$_{32}$N$_2$O$_2$ (M$^+$+H): 416.254. found 416.249.

Diagnostic $^1$H-NMR peaks for minor isomer 35: 6.49 (s, 1H), 4.85 (td, J=11.1 Hz, 1H).

6-Cyano-17-(3-pyridyl)-androst-6,16-dien-3β-ol (37) and 6-Cyano-17-(3-pyridyl)-androst-5,16-dien-3β-ol (38)

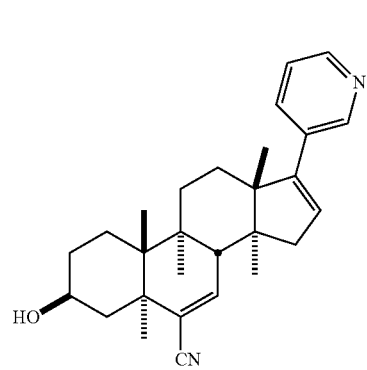

37

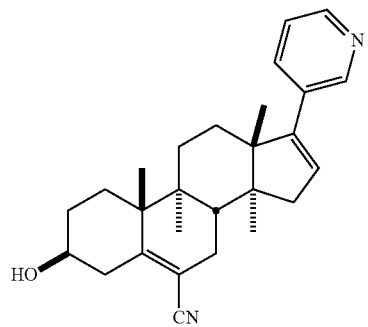

38

The mixture of isomers (20 mg; 1:5 35 to 36) was deacylated as described for 5. The resulting mixture (12 mg, 67%) was purified by preparative HPLC to obtain 1.2 mg of 37 and 1.5 mg of 38, both as white solids.

Data for 37: IR (neat) 3322, 2210, 1465, 1445, 1420, 1378 cm$^{-1}$; $^1$H NMR (500 MHz, CDCl$_3$) δ 8.63 (s, 1H), 8.50 (s, 1H), 7.72 (dt, J=8.1, 1.9 Hz, 1H), 7.32 (d, J=6.6 Hz, 1H), 6.56 (t, J=2.7 Hz, 1H, the diagnostic peak of 7-H), 6.12-5.94 (m, 1H), 3.70 (tt, J=10.6, 4.9 Hz, 1H), 2.39 (m, 2H), 2.30-2.15 (m, 2H), 2.15-2.00 (m, 2H), 1.91-1.76 (m, 2H), 1.69 (m, 2H), 1.59 (m, 1H), 1.53-1.36 (m, 2H), 1.28-1.18 (m, 1H), 1.18-1.09 (m, 1H), 1.05 (s, 3H), 0.86 (s, 3H); $^{13}$C NMR (126 MHz, CDCl$_3$) δ 151.1, 149.0, 147.0, 146.7, 134.8, 129.5, 124.1, 123.5, 118.1, 116.2, 70.7, 54.5, 51.5, 48.4, 44.7, 41.0, 37.5, 34.9, 34.4, 33.5, 31.3, 30.6, 20.8, 16.7, 11.7; HRMS calculated for C$_{25}$H$_{30}$N$_2$O (M$^+$+H): 375.2436. found 375.2414.

Data for 38: IR (neat) 3318, 2211, 1454, 1445, 1412, 1376 cm$^{-1}$; $^1$H NMR (500 MHz, CDCl$_3$) δ 8.63 (s, 1H), 8.50 (s, 1H), 7.74 (dt, J=8.0, 1.9 Hz, 1H), 7.32 (dd, J=8.0, 4.9 Hz, 1H), 6.06 (dd, J=3.3, 1.8 Hz, 1H), 3.65 (tt, J=11.1, 4.5 Hz, 1H), 3.14 (m), 2.45-2.25 (m, 3H), 2.22-2.03 (m, 3H), 2.03-1.91 (m, 3H), 1.83 (m, 2H), 1.71 (m, 1H), 1.67-1.58 (m, 3H), 1.58-1.46 (m, 1H), 1.15 (s, 3H), 1.06 (s, 3H); $^{13}$C NMR (126 MHz, CDCl$_3$) δ 159.0, 150.9, 146.7, 146.5, 134.9, 133.2, 129.9, 123.6, 118.9, 106.4, 70.5, 56.8, 49.1, 47.2, 41.0, 40.3, 36.3, 34.9, 33.5, 31.7, 30.6, 29.7, 20.7, 19.6, 16.5; HRMS calculated for C$_{25}$H$_{30}$N$_2$O (M$^+$+H): 375.2436. found 375.2424.

3β-Acetoxy-6-nitro-Δ5-androst-5-en-17-one (39)

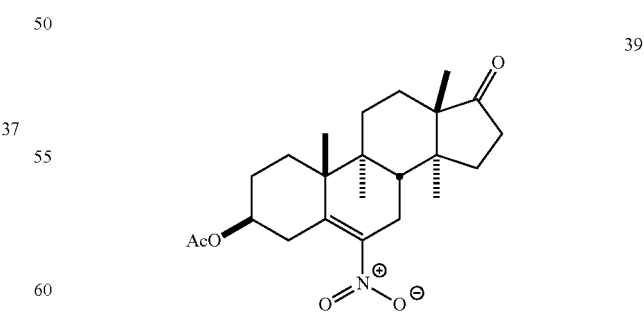

39

Compound 2 (150 mg, 0.453 mmol) was dissolved in dry diethyl ether and cooled to 0° C. under inert atmosphere. Fuming nitric acid was slowly added over 1 h (2.25 mL, 5% w/v). After stirring an additional 1.5 h at 0° C., cold water (4 mL) was slowly added. The mixture was diluted with ether (15 mL), the organic layer separated and washed with water, two washes of saturated aqueous sodium bicarbonate, brine, and dried over NaSO$_4$. The crude material was purified by automated purification system (4 g silica, 10% to 35% EtOAc/hexanes) to yield 61 mg of a yellow powder (36%). This analytical data matched that reported for this compound.

3β-Acetoxy-6-nitro-17-triflyl-androst-5,16-diene

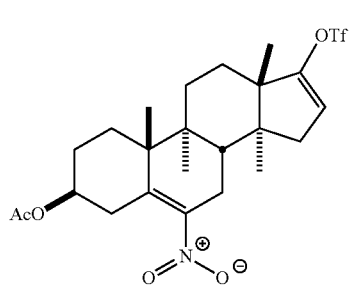

Compound 39 (61 mg, 0.163 mmol) was triflated as described for 3. This material was purified by silica flash chromatography (300 mg silica, 20% EtOAc/hexanes) to obtained 57 mg of 39 as a white solid (48%). $^1$H NMR (400 MHz, CDCl$_3$) δ 5.63 (dd, J=3.4, 1.7 Hz, 1H), 4.67 (tt, J=11.6, 4.5 Hz, 1H), 2.85 (m, 1H), 2.57 (m, 1H), 2.38-2.19 (m, 3H), 2.11 (m, 1H), 2.06 (s, 3H), 2.03-1.96 (m, 2H), 1.98-1.83 (m, 2H), 1.82-1.47 (m, 6H), 1.32 (m, 1H), 1.21 (s, 3H), 1.03 (s, 3H); $^{13}$C NMR (101 MHz, CDCl$_3$) δ 170.1, 158.6, 145.8, 138.2, 114.4, 71.7, 53.5, 49.2, 44.6, 38.0, 36.0, 32.4, 32.1, 31.2, 29.7, 28.5, 26.9, 21.2, 20.1, 19.6, 15.0.

3β-Acetoxy-6-nitro-17-(3-pyridyl)-androst-5,16-diene (40)

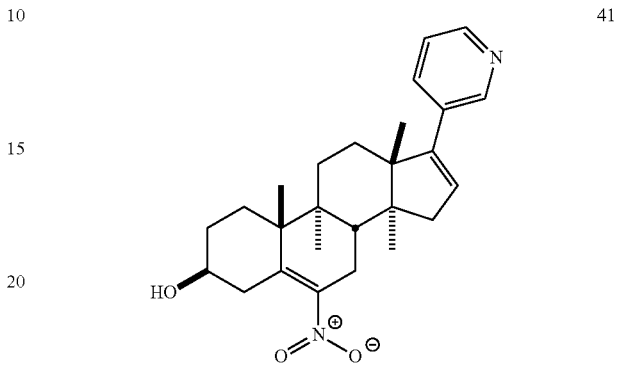

The above compound (57 mg, 0.113 mmol) was coupled as described for 4. This material was purified by silica flash chromatography (200 mg silica, 50% EtOAc/hexanes) to isolate 27 mg of 40 as a white solid (51%). IR (neat): 1742, 1631, 1518, 1456, 1363 cm$^{-1}$; $^1$H NMR (400 MHz, CDCl$_3$) δ 8.71-8.58 (m, 1H), 8.51 (dd, J=4.8, 1.6 Hz, 1H), 7.68 (dt, J=8.0, 2.0 Hz, 1H), 7.29-7.24 (m, 1H), 6.04 (dd, J=3.3, 1.8 Hz, 1H), 4.69 (tt, J=11.6, 4.5 Hz, 1H), 2.85 (m, 1H), 2.61 (m, 1H), 2.32 (m, 4H), 2.21-2.10 (m, 2H), 2.06 (s, 3H), 2.04-1.88 (m, 3H), 1.86-1.45 (m, 6H), 1.43-1.26 (m, 2H), 1.23 (s, 3H), 1.08 (s, 3H); $^{13}$C NMR (101 MHz, CDCl$_3$) δ 170.1, 151.2, 147.9, 147.6, 146.3, 137.9, 134.0, 132.7, 129.1, 123.2, 71.8, 56.7, 49.1, 47.3, 38.0, 36.1, 34.9, 33.0, 31.6, 31.2, 30.2, 27.0, 21.2, 20.8, 19.7, 16.5; MS calculated for C$_{26}$H$_{32}$N$_2$O$_4$ (M$^+$+H): 437.244. found 437.300.

6-Nitro-17-(3-pyridyl)-androst-5,16-dien-3β-ol (41)

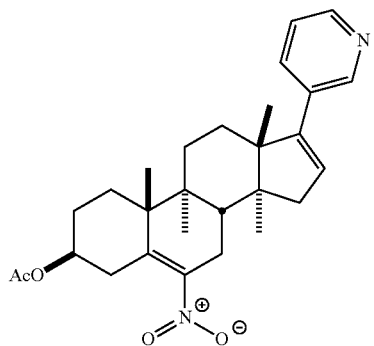

Compound 40 (27 mg, 0.061 mmol) was deacylated as for 5. 15 mg (82%) was isolated by chromatography (50% EtOAc/hexanes). This was further purified by preparative HPLC to obtain 6 mg. IR (neat): 3330, 1547, 1518, 1440, 1376, 1351 cm$^{-1}$; $^1$H NMR (500 MHz, CDCl$_3$) δ 8.56 (s, 1H), 8.43 (s, 1H), 7.65 (dt, J=8.0, 1.7 Hz, 1H), 7.24 (s, 1H), 5.97 (dd, J=3.3, 1.8 Hz, 1H), 3.57 (tt, J=11.3, 4.6 Hz, 1H), 2.74 (m, 1H), 2.32-2.15 (m, 2H), 2.15-179 (m, 6H), 1.66 (m, 1H), 1.64-1.37 (m, 4H), 1.23-1.16 (m, 1H), 1.12 (s, 3H), 0.99 (s, 3H); $^{13}$C NMR (126 MHz, CDCl$_3$) δ 150.94, 145.82, 138.90, 134.64, 132.14, 129.66, 128.56, 128.46, 123.45, 70.16, 56.77, 49.22, 41.01, 37.96, 36.52, 35.17, 34.86, 32.94, 31.67, 30.50, 30.17, 20.78, 19.60, 16.50; HRMS calculated for C$_{24}$H$_{30}$N$_2$O$_3$ (M$^+$+H): 395.2334. found 395.2343.

3β-Hydroxy-17-(3-pyridyl)-androst-5,16-dien-6-amide (42)

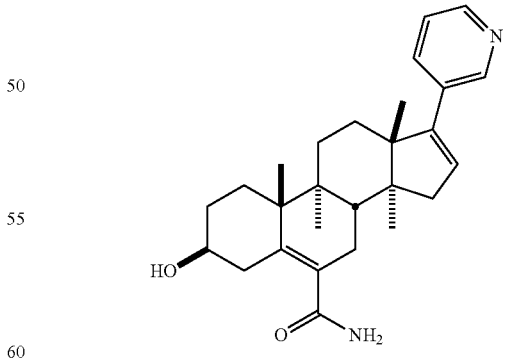

Compound 38 (30 mg, 0.079 mmol) was added to a microwave vial, dissolved in dimethylsulfoxide (2.6 mL, 0.03 M), and cooled to 0° C. Potassium carbonate (109 mg, 0.788 mmol) was added, followed by hydrogen peroxide (0.5 mL of 30% aqueous solution). The mixture was immediately capped and stirred for 48 h, warming to rt. The base was quenched with aqueous 2 N HCl and the DMSO/H$_2$O frozen and lyophilized off. The resulting solid was redissolved in water and extracted with chloroform, washed with brine, and dried over NaSO$_4$. The crude mixture was purified by column (250 mg silica, 1% MeOH/DCM to 5% MeOH/DCM) to obtain 12.1 mg of a white solid (39%). This was further subjected to preparative HPLC to obtain 3.5 mg of a fluffy white powder. IR (neat) 3344, 1658, 1597, 1426, 1408, 1377, 1335 cm$^{-1}$; $^1$H NMR (500 MHz, CDCl$_3$) δ 8.57 (s, 1H), 8.44 (s, 1H), 7.82 (dd, J=16.3, 7.2 Hz, 1H), 7.39 (s, 1H), 6.11-6.01 (m, 1H), 3.45 (ddt, J=11.3, 8.3, 4.2 Hz, 1H), 3.40-3.29 (m, 1H), 2.24 (dtd, J=14.9, 8.8, 7.7, 4.7 Hz, 2H), 2.16-1.94 (m, 3H), 1.94-1.70 (m, 4H), 1.70-1.32 (m, 7H), 1.18 (s, 5H), 1.10-1.02 (m, 3H), 0.98 (d, J=3.7 Hz, 3H), 0.94-0.67 (m, 4H); $^{13}$C NMR (126 MHz, CDCl$_3$) δ 175.3, 151.0, 146.9, 139.8, 134.5, 132.3, 131.0, 129.8, 128.4, 123.5, 70.6, 57.1, 47.2, 40.4, 37.4, 36.8, 35.0, 33.3, 31.7, 30.5, 29.8, 29.7, 20.7, 19.4, 16.5; HRMS calculated for C$_{25}$H$_{33}$N$_2$O$_2$ (M$^+$+1): 393.2537. found 393.2525.

Enzyme Activity Assays

Complementary assays were utilized for the quantitative comparison of compound activity data for CYP17A1 and CYP21A2. Progesterone is a substrate for both CYP17A1 and CYP21A2, and was the substrate studied for enzyme activity, IC$_{50}$ determinations, and selectivity comparison. Two methods for detecting enzymatic activity were utilized. Analytical High Pressure Liquid Chromatography (HPLC) for biochemical assays was performed on a Prominence HPLC system (Shimadzu Scientific Instruments, Inc., Columbia, Md.) equipped with a C18 reverse phase 100 mm Luna Column (Phenomenex, Torrance, Calif.). The mobile phase consisted of 40% acetonitrile, 59% water, and 1% acetic acid with a 1 mL/min flow rate at 40° C. An injection volume of 32 μL (CYP17A1) or 45 μL (CYP21A2) was used. The presence of the CYP17A1 product 17α-hydroxyprogesterone was detected with an absorption wavelength of 248 nm as reported by Devore, N. M.; Scott, E. E. Structure and function of human cytochromes P450 enzymes: Xenobiotic metabolism by CYP2A and steroid biosynthesis by CYP17A1. University of Kansas, Lawrence, K S, 2011. The presence of the CYP21A2 product 21-hydroxyprogesterone was detected with an absorption wavelength of 248 nm.

Modified constructs of human CYP17A1, human CYP21A2, and human NADPH-cytochrome P450 oxidoreductase (POR) were used. These protein constructs lack a hydrophobic N-terminal transmembrane helix. The resulting proteins are still expressed in a membrane-bound form, but can be more easily extracted and solubilized with detergents, facilitating their crystallization and functional analysis. Specifically, this modification allows their study as purified proteins rather than as components in a less-defined preparation of microsomes. Thus, the absolute concentrations of each P450 as well as POR are known, rather than concentrations relative to total protein content as used in typical assays for CYP17A1 and CYP21A2 activity in the literature. See, e.g., Roelofs, M. J.; Piersma, A. H.; van den Berg, M.; van Duursen, M. B. The relevance of chemical interactions with CYP17 enzyme activity: assessment using a novel in vitro assay. *Toxicol. Appl. Pharmacol.* 2013, 268, 309-317; Imai, T.; Globerman, H.; Gertner, J. M.; Kagawa, N.; Waterman, M. R. Expression and purification of functional human 17 alpha-hydroxylase/17,20-lyase (P450c17) in *Escherichia coli*. Use of this system for study of a novel form of combined 17 alpha-hydroxylase/17,20-lyase deficiency. *J. Biol. Chem.* 1993, 268, 19681-19689; Dhir, V.; Ivison, H. E.; Krone, N.; Shackleton, C. H.; Doherty, A. J.; Stewart, P. M.; Arlt, W. Differential inhibition of CYP17A1 and CYP21A2 activities by the P450 oxidoreductase mutant A287P. *Mol. Endocrinol.* 2007, 21, 1958-1968.

The specific CYP17A1 construct utilized, CYP17A1A19H, was generated from the wild type sequence of human CYP17A1, as reported by DeVore. The additional A19 and H signify an N-terminal deletion of 19 amino acids for solubility (the "A19") and a C-terminal four-histidine tag for purification (the "H"). Hereafter in the discussion of the assays below, "CYP17A1" will refer to CYP17A1HΔ19 for simplicity. "Full-length CYP17A1" will be specifically designated when appropriate.

The CYP21A2 construct that was used, CYP21A2dH, was also engineered as according to published procedures. See, e.g., Blake, L. C.; Scott, E. E. Cytochromes P450 as therapeutic targets and counter-targets for the prevention of lung cancer and treatment of steroidogenic diseases. University of Kansas, Lawrence, K S, 2012. In this construct, the "d" refers to an 18 amino acid N-terminal deletion. An N-terminal solubility tag was added, in addition to a C-terminal four-histidine tag ("H"). Hereafter in the discussion of the assays below, "CYP21A2" will refer to CYP21A2dH for simplicity. "Full-length CYP21A2" will be specifically designated when appropriate.

The human POR construct utilized bears an N-terminal truncation of a transmembrane helix (Δ27) to increase expression levels, and a K59Q mutation to prevent proteolysis. This POR construct was overexpressed and purified following the procedure reported in Sandee, D.; Miller, W. L. High-yield expression of a catalytically active membrane-bound protein: human P450 oxidoreductase. *Endocrinology* 2011, 152, 2904-2908.

GC/MS was performed on an Agilent Technologies 6850 Network GC System equipped with a 6850 series autosampler and an Agilent Technologies 5975C VL MSD with triple axis detector. The electron energy was 70 eV and the ion source temperature was 230° C. Each sample (5 μL) was injected at an injector temperature of 280° C. and separated through an Ultra-1 capillary column (25 m×0.2 mm inner diameter, 0.33-mm film thickness; Agilent Technologies). The oven temperature was initially 215° C., which was ramped to 245° C. at 1° C./min and then finally increased to 315° C. and held for 2 minutes, using a 10° C./min ramping program. Helium was used as the carrier gas with a column head pressure of 210.3 kPa (column flow: 1.0 mL/min at an oven temperature of 215° C.). For quantitative analysis, the characteristic ions of the monitored steroids were determined as their poly-TMS derivatives. Product and starting material MS counts were normalized for analysis against a known amount of estriol internal standard.

Samples were prepared for GC/MS by solid phase extraction (SPE) using SUPELCO Supel™-Select HLB SPE tubes, bed weight 30 mg (Sigma Aldrich). Parallel evaporation was performed using a GeneVac EZ-2 plus evaporator. Poly-trimethylsilyl derivatization was accomplished using a 1000:8:4 (v/w/w) N-methyl-N-(trimethylsilyl) trifluoroacetamide:ammonium iodide:dithioerythritol mixture that had been stirred at room temperature for at least 12 hours (MSTFA).

Changes in absorbance or GC/MS counts were analyzed using Prism (GraphPad Software). Enzyme activity data was fit to the Michaelis-Menten equation to determine the steady state kinetic parameters. Product formation data was fit to the variable slope inhibition equation $Y=100/(1+10^{((Log IC50-X)*HillSlope)})$ in Prism 5 (GraphPad, La Jolla, Calif.) to determine inhibitor IC$_{50}$ values. Data from at least two replicates with 8 or more activity points each were averaged and analyzed for standard error.

Analysis of 17α-Hydroxyprogesterone Generation by CYP17A1 Using HPLC

The assays were carried out with 50 pmol of purified CYP17A1 in a 1:4 ratio with POR. The protein stocks were gently mixed together by pipetting and incubated on ice for 20 minutes. This reconstituted protein system was added to buffer (50 mM Tris, pH 7.4 and 5 mM $MgCl_2$) containing progesterone (0-50 μM) for a total volume of 500 μL. For the inhibition studies, 50 μM progesterone was used. The samples were incubated at 37° C. for 3 minutes. Reactions were initiated by the addition of 1 mM NADPH. Reactions were allowed to proceed for ten minutes at 37° C. and stopped by the addition of 300 μL of 20% TCA and placed on ice. All standards (consisting of 17α-hydroxyprogesterone in assay conditions) and zero samples had 300 μL of 20% trichloroacetic acid (TCA) added prior to the addition of NADPH. Samples and standards were centrifuged at 5000×g for 10 minutes to pellet out the protein. The presence of 17α-hydroxyprogesterone was detected with an absorption wavelength of 248 nm. 17α-hydroxyprogesterone eluted at approximately 5.5 minutes.

The CYP17A1 progesterone hydroxylation inhibitory activities of the clinical compounds abiraterone (5), galaterone, and orteronel were measured along with certain compounds of the present technology. The results are provided in Table 1, where CYP17A1 $IC_{50}$ results are provided along with the standard error.

TABLE 1

| Compound | CYP17A1 $IC_{50}$ (nM) |
| --- | --- |
| abiraterone (5) | 130 ± 7 |
| galaterone | 282 ± 16 |
| orteronel | 4,730 ± 139 |
| 8 | 428 ± 20 |
| 21 | 1,380 ± 50 |
| 29 | 208 ± 12 |

TABLE 1-continued

| Compound | CYP17A1 IC$_{50}$ (nM) |
|---|---|
| 30 | 5,410 ± 374 |
| 31 | 199 ± 13 |
| 32 | 3,970 ± 240 |
| 33 | 150 ± 10 |
| 37 | 244 ± 14 |
| 38 | 174 ± 8 |
| 41 | 183 ± 23 |
| 42 | 120 ± 12 |

Among the clinical compounds, orteronel was significantly less potent than either abiraterone (5) or galaterone, potentially due to its reported selectivity for CYP17A1 lyase over CYP17A1 hydroxylase activity. See Yamaoka, M.;

Hara, T.; Hitaka, T.; Kaku, T.; Takeuchi, T.; Takahashi, J.; Asahi, S.; Miki, H.; Tasaka, A.; Kusaka, M. Orteronel (TAK-700), a novel non-steroidal 17,20-lyase inhibitor: Effects on steroid synthesis in human and monkey adrenal cells and serum steroid levels in cynomolgus monkeys. *The Journal of Steroid Biochemistry and Molecular Biology* 2012, 129, 115-128. All tested compounds of the present technology exhibited CYP17A1 hydroxylase activity.

Analysis of 21-Hydroxyprogestone Generation by CYP21A2 Using GC/MS.

The assays were carried out with 20 pmol of purified CYP21A1 in a 1:4 ratio with POR. The protein stocks were gently mixed together by pipetting and incubated on ice for 20 minutes. This reconstituted protein system was added to buffer (50 mM Tris, pH 7.4 and 5 mM MgCl$_2$) containing analytes (0-2 μM) for a total volume indicated above. For the inhibition studies, 0.5 μM progesterone was used as the substrate concentration for inhibition studies. Control reactions were pre-quenched by the addition of 300 μL of 20% trichloroacetic acid [containing 34.64 μg/mL estriol internal standard] and placed on ice before the NADPH addition. Reactions were quenched 10 minutes after the addition of NADPH by the same (internal standard-containing) solution, and allowed to stand on ice for 10 minutes.

Solid phase extraction (SPE) cartridges (30 mg HLB resin, Sigma-Aldrich) were used on a parallel draining rack. SPEs were pre-equilibrated with 2×1 mL hexanes, 2×1 mL acetone, and 3×1 mL deionized water. Reaction samples (750 μL) were loaded onto individual SPE cartridges, allowed to drain, and then washed with 1 mL water. Glass vials (4 mL capacity) were placed under each tube, and samples were eluted with 4×1 mL acetone. The vials were concentrated for at least 12 hours by parallel evaporation to remove solvent and residual water. MSTFA derivatizing agent (120 μL) was added to each sample vial, which was capped and heated to 60° C. for 60 minutes, stirring by hand intermittently.

The amount of 21-hydroxyprogesterone present was determined by GC-MS analysis using single ion monitoring (M/Z 546.35, ca. 26 min retention time), and analyzed against the estriol internal standard peak (M/Z 504.30, ca. 15 min retention time). Progesterone (M/Z 458.30, ca. 16 min retention time) was detected for quality control among reactions and standards. For instance, if a sample registered no product or standard peak as well as no progesterone peak, it was discarded from analysis due to experimental error.

Determination of CYP21A2 IC$_{50}$ Values and Selectivity for CYP17A1 Over CYP21A2

The CYP21A2 inhibitory activity profiles of selected compounds of the present technology were determined alongside the clinical compounds abiraterone (5), galaterone, and orteronel as illustrated in Table 2 using the conditions described above. Inhibitory activity was measured as a percentage of the maximal CYP21A2 activity, which was determined with inhibitor-free reactions run alongside each series of inhibitor concentrations. The CYP21A2 IC$_{50}$ data includes the analyzed results along with the standard error. The selectivity factor (17A1/21A2 Sel. Factor) was calculated by dividing each compound's CYP21A2 IC$_{50}$ by its CYP17A1 IC$_{50}$.

TABLE 2

| Compound | CYP21A2 IC$_{50}$ (nM) | 17A1/21A2 Sel. Factor |
|---|---|---|
| 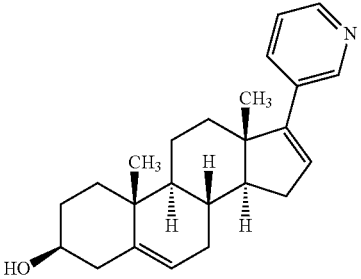 abiraterone (5) | 296 ± 26 | 2.3 |
| 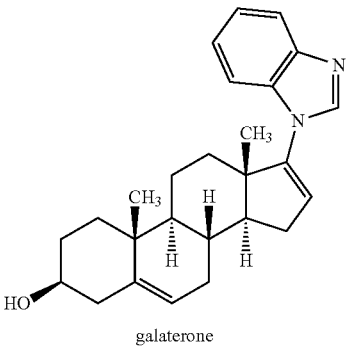 galaterone | 248 ± 24 | 0.9 |
| 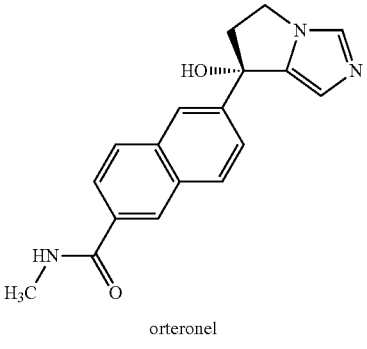 [SMILES: CNC(=O)c1ccc2cc([C@@]3(O)CCn4cncc43)ccc2c1] orteronel | 4,870 ± 476 | 1.0 |
| 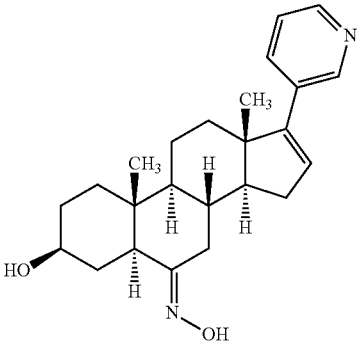 33 | 10,300 ± 582 | 68.9 |

TABLE 2-continued

| Compound | CYP21A2 IC$_{50}$ (nM) | 17A1/21A2 Sel. Factor |
|---|---|---|
| 38 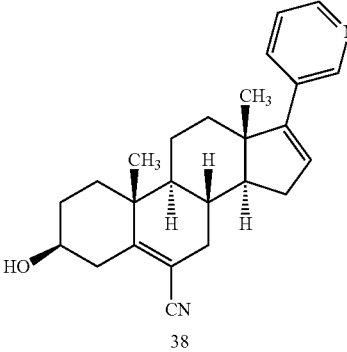 | 537 ± 52 | 3.1 |
| 29 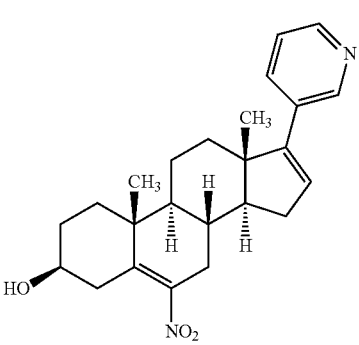 | 831 ± 96 | 4.5 |
| 42 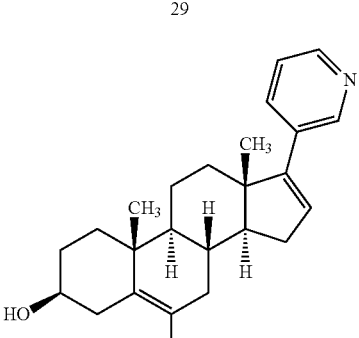 | 8,700 ± 912 | 72.2 |

As illustrated in Table 2, each of the clinical agents demonstrated IC$_{50}$ values for CYP21A2 similar to their CYP17A1 IC$_{50}$, where abiraterone was the most selective of these clinical agents—2.3-fold more effective in inhibiting CYP17A1 progesterone 17α-hydroxylation activity than CYP21A2 progesterone 21-hydroxylation. While the CYP17A1 potencies of compounds 33, 38, 41, and 42 of the present technology are roughly comparable to abiraterone (IC$_{50}$ 120-183 nM vs. 130 nM, respectively; Table 1 above), these compounds of the present technology exhibit increased selectivity for CYP17A1 over CYP21A2 inhibition. Compounds 33 and 42 displayed the highest selectivity with selectivity factors of 68.9 and 72.2, respectively. Thus, each of the tested compounds of the present technology exhibited a higher CYP17A1/CYP21A2 selectivity than the most selective clinical agent tested (abiraterone), with compounds 33 and 42 exhibiting a CYP17A1/CYP21A2 selectivity about 30 times greater than abiraterone.

In Vivo Evaluation of Compounds of Present Technology

In vivo studies will involve initially dosing mice with abiraterone to establish a baseline, examining the effect of the drug on select agents on levels of both androgen (mainly testosterone and dihydrotestosterone) and adrenal, or glucocorticoid/mineralcorticoid (11-deoxycortisol, cortisol, cortisone, aldosterone) steroids. An analogous study will then be performed with compounds of the present technology. It is expected that compounds of the present technology will inhibit CYP17A1 hydroxylase activity in mice and will not significantly co-inhibit adrenal hormone biosynthesis. Such a profile will further evidence the utility of compounds of the present technology in treating cancers such as prostate cancer in a way that is distinct to selectively inhibiting the lyase activity of CYP17A1.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A compound according to formula I or II

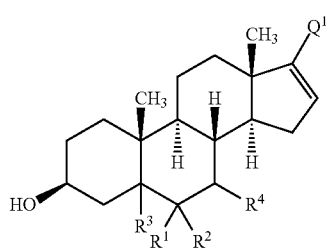

(I)

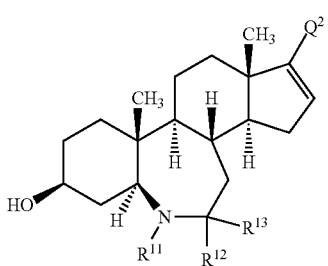

(II)

or a salt thereof, or a tautomer thereof, or a solvate thereof, wherein $Q^1$ is

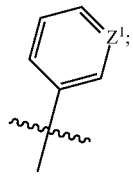

$Q^2$ is

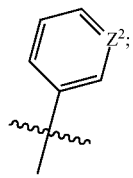

$R^1$ and $R^2$ are each independently H, OH, C(O)NR$^{27}$R$^5$, C(O)OR$^6$, NR$^7$R$^8$, trifluoromethyl, trifluoromethoxy, halo, nitro, cyano, or a substituted or unsubstituted alkoxy, aryloxy, arylalkoxy, or alkanoyloxy group provided that $R^1$ and $R^2$ are not both H, or $R^1$ and $R^2$ together are =O, =N—OH, or =N—NHR$^9$;

$R^3$ is H, or $R^1$ and $R^3$ together are O, NR$^9$, S, S(O), S(O)$_2$, or a bond, provided that when $R^1$ and $R^3$ together are not NR$^9$ or a bond then $R^2$ is not NR$^7$R$^8$;

$R^4$ is H, or $R^1$ and $R^4$ together are O, NR$^{10}$, S, S(O), S(O)$_2$, or a bond, provided that when $R^1$ and $R^3$ together are not NR$^{10}$ or a bond then $R^2$ is not NR$^7$R$^8$;

$Z^1$ and $Z^2$ are each independently CH or N;

$R^{27}$, $R^5$, $R^7$, $R^8$, $R^9$, and $R^{10}$ are each independently H or a substituted or unsubstituted alkyl, cycloalkyl, cycloalkylalkyl, alkanoyl, aryl, aralkyl, heterocyclyl, heteroaryl, heterocyclylalkyl, or heteroaralkyl group;

$R^6$ is independently at each occurrence H or a substituted or unsubstituted alkyl, cycloalkyl, cycloalkylalkyl, aryl, aralkyl, heterocyclyl, heteroaryl, heterocyclylalkyl, or heteroaralkyl group;

$R^{11}$ is H or a substituted or unsubstituted cycloalkyl, cycloalkylalkyl, alkanoyl, aryl, aralkyl, heterocyclyl, heteroaryl, heterocyclylalkyl, or heteroaralkyl group; and $R^{12}$ and $R^{13}$ are each H or together are =O, provided that $R^{12}$ and $R^{13}$ together are not =O when $R^{11}$ is H; or $R^{11}$, $R^{1-2}$, and $R^{13}$ together are —N=N—N=;

with the proviso that where $Z^1$ is N, $R^1$ and $R^3$ together are a bond, and $R^4$ is H, then $R^2$ is not H.

2. The compound of claim 1, wherein $Z^1$ and $Z^2$ are each N.

3. The compound of claim 1, wherein the compound of formula I is a compound of formula III, IV, or V

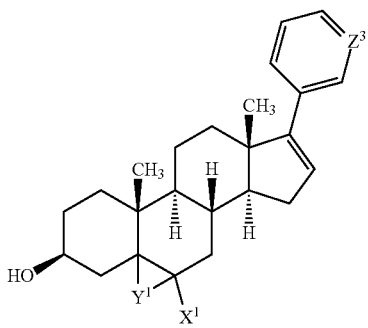

(III)

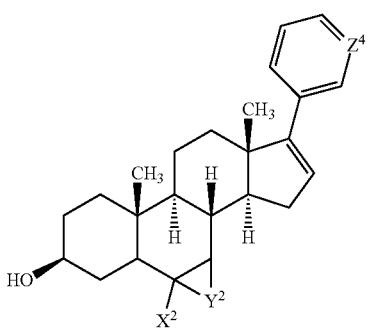

(IV)

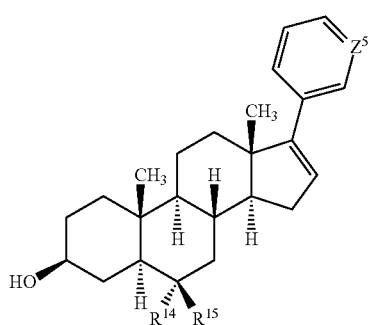

(V)

or a salt thereof, or a tautomer thereof, or a solvate thereof, wherein
- $X^1$ and $X^2$ are each independently H, $C(O)NR^{16}R^{17}$, $C(O)OR^{18}$, $NR^{19}R^{20}$, trifluoromethyl, halo, nitro, or cyano;
- $Y^1$ and $Y^2$ are each independently O, $NR^{21}$, S, S(O), $S(O)_2$, or a bond, provided that when $Y^1$ and $Y^2$ are not $NR^{21}$ or a bond then $X^1$ and $X^2$ are not $NR^{19}R^{20}$,
- $Z^3$, $Z^4$, and $Z^5$ are each independently CH or N;
- $R^{14}$ and $R^{15}$ are each independently H, OH, $NR^{22}R^{23}$, trifluoromethoxy, or a substituted or unsubstituted alkoxy, aryloxy, arylalkoxy, or alkanoyloxy, group provided that $R^{14}$ and $R^{15}$ are not both H;
- or $R^{14}$ and $R^{15}$ together are =O, =N—OH, or =N—$NHR^{24}$;
- $R^{16}$, $R^{17}$, $R^{19}$, $R^{20}$, $R^{21}$, $R^{22}$, $R^{23}$, and $R^{24}$ are each independently H or a substituted or unsubstituted alkyl, cycloalkyl, cycloalkylalkyl, alkanoyl, aryl, aralkyl, heterocyclyl, heteroaryl, heterocyclylalkyl, or heteroaralkyl group; and
- $R^{18}$ is H or a substituted or unsubstituted alkyl, cycloalkyl, cycloalkylalkyl, aryl, aralkyl, heterocyclyl, heteroaryl, heterocyclylalkyl, or heteroaralkyl group;
with the proviso that when $Z^3$ is N and $Y^1$ is a bond then $X^1$ is not H.

4. The compound of claim 3, wherein $Z^3$, $Z^4$, and $Z^5$ are each independently N.

5. The compound of claim 3, wherein
- $Y^1$ is O or a bond;
- $Y^2$ is a bond; and
- $X^1$ and $X^2$ are each independently $C(O)NR^{16}R^{17}$, $C(O)OR^{18}$, nitro, or cyano.

6. The compound of claim 3, wherein $R^{14}$ and $R^{15}$ are each independently H, OH, $NR^{22}R^{23}$, or trifluoromethoxy; or $R^{14}$ and $R^{15}$ together are =O or =N—OH.

7. The compound of claim 1, wherein the compound of formula II is a compound of formula VI, VII, or VIII

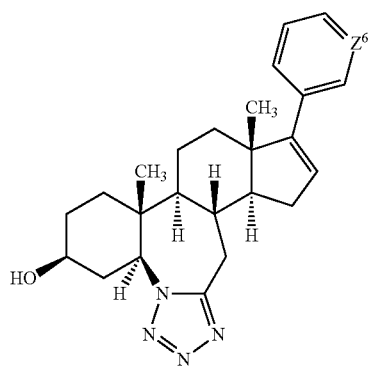

(VI)

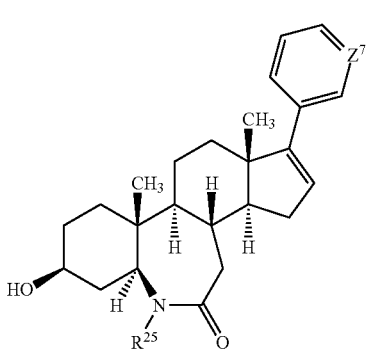

(VII)

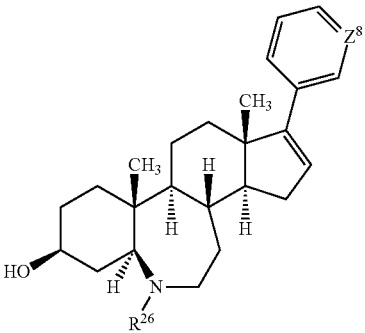

(VIII)

or a salt thereof, or a tautomer thereof, or a solvate thereof, wherein
- $Z^6$, $Z^7$, and $Z^8$ are each independently CH or N;
- $R^{25}$ is H or a substituted or unsubstituted cycloalkyl, cycloalkylalkyl, alkanoyl, aryl, aralkyl, heterocyclyl, heteroaryl, heterocyclylalkyl, or heteroaralkyl group; and
- $R^{26}$ is a substituted or unsubstituted cycloalkyl, cycloalkylalkyl, alkanoyl, aryl, aralkyl, heterocyclyl, heteroaryl, heterocyclylalkyl, or heteroaralkyl group.

8. The compound of claim 7, wherein the compound of formula II is a compound according to formula VI.
9. The compound of claim 1, wherein the compound is
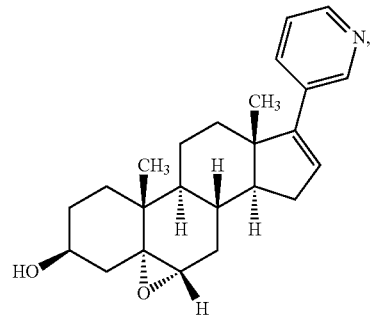
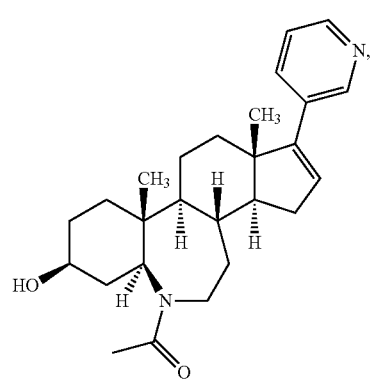
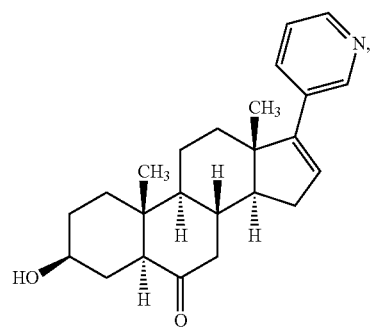
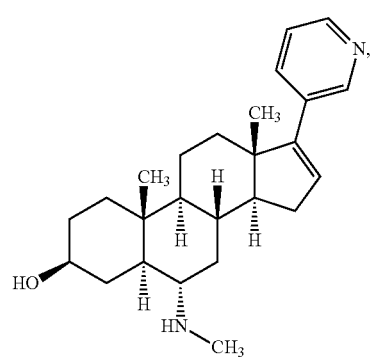
-continued
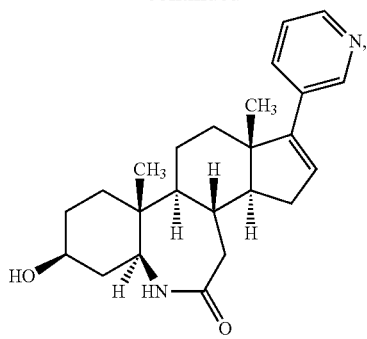
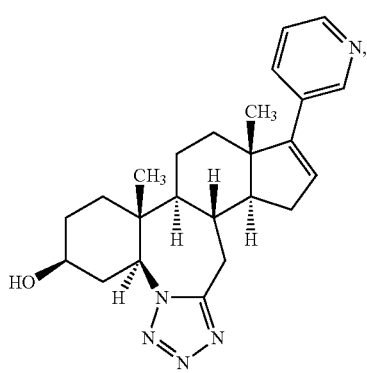
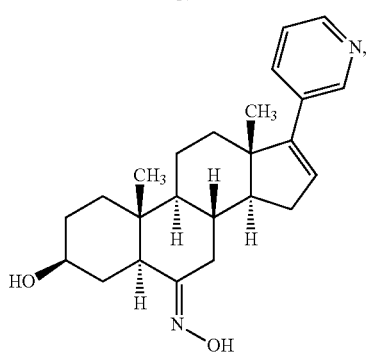
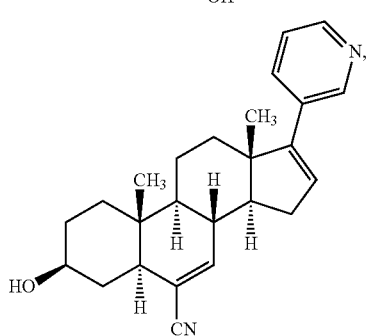
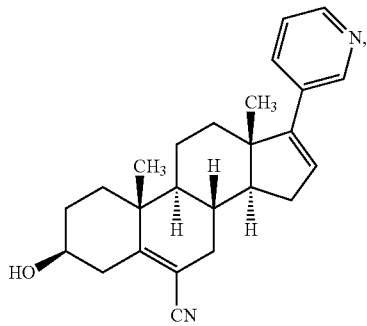

-continued

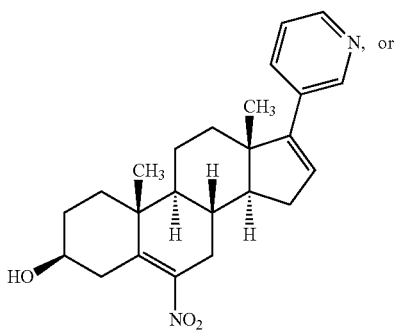

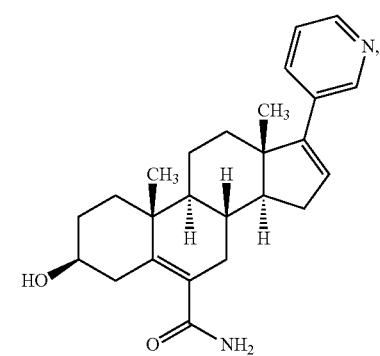

or a salt thereof, or a tautomer thereof, or a solvate thereof.

10. A pharmaceutical composition, comprising an effective amount of the compound of claim 2 and a pharmaceutically acceptable carrier.

11. A method comprising inhibiting CYP17A1 by administration of the compound of claim 2.

12. The method of claim 11, comprising inhibiting CYP17A1 by administration of a pharmaceutical composition wherein the pharmaceutical composition comprises an effective amount of the compound and a pharmaceutically acceptable carrier.

13. The method of claim 11, wherein administration of the compound selectively inhibits CYP17A1.

14. The method of claim 13, wherein administration of the compound selectively inhibits CYP17A1 over CYP21A2.

15. The method of claim 11, wherein the compound is of formula III or V

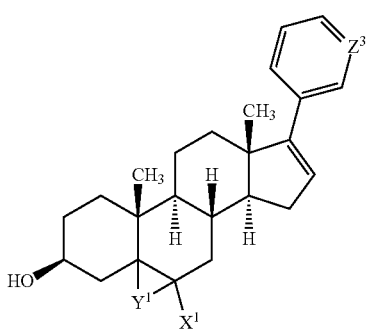

(III)

-continued

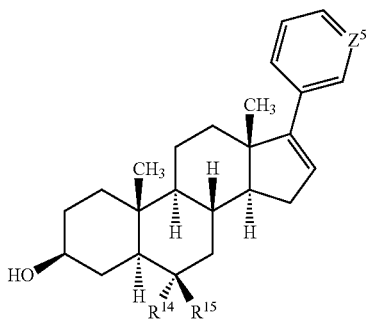

(V)

or a salt thereof, or a tautomer thereof, or a solvate thereof, wherein $X^1$ is H, $C(O)NR^{16}R^{17}$, $C(O)OR^{18}$, $NR^{19}R^{20}$, trifluoromethyl, halo, nitro, or cyano;

$Y^1$ is O, $NR^{21}$, S, $S(O)$, $S(O)_2$, or a bond, provided that when $Y^1$ is not $NR^{21}$ or a bond then $X^1$ is not $NR^{19}R^{20}$;

$Z^3$ and $Z^5$ are each independently N;

$R^{14}$ and $R^{15}$ are each independently H, OH, $NR^{22}R^{23}$, trifluoromethoxy, or a substituted or unsubstituted alkoxy, aryloxy, arylalkoxy, or alkanoyloxy, group provided that $R^{14}$ and $R^{15}$ are not both H;

or $R^{14}$ and $R^{15}$ together are =O, =N—OH, or =N—$NHR^{24}$;

$R^{16}$, $R^{17}$, $R^{19}$, $R^{20}$, $R^{21}$, $R^{22}$, $R^{23}$, and $R^{24}$ are each independently H or a substituted or unsubstituted alkyl, cycloalkyl, cycloalkylalkyl, alkanoyl, aryl, aralkyl, heterocyclyl, heteroaryl, heterocyclylalkyl, or heteroaralkyl group; and $R^{18}$ is H or a substituted or unsubstituted alkyl, cycloalkyl, cycloalkylalkyl, aryl, aralkyl, heterocyclyl, heteroaryl, heterocyclylalkyl, or heteroaralkyl group;

with the proviso that when $Z^1$ is N and $Y^1$ is a bond then $X^1$ is not H.

16. A method of treating a biological condition comprising administering to a subject suffering from a biological condition selected from leukemia, colon cancer, breast cancer, or prostate cancer, an effective amount of the compound of claim 2.

17. The method of claim 16, wherein the method comprises administering a pharmaceutical composition, wherein the pharmaceutical composition comprises the effective amount of the compound and a pharmaceutically acceptable carrier.

18. The method of claim 16, wherein the biological condition is breast cancer or prostate cancer.

19. The method of claim 16, wherein the compound is of formula III or V (III)

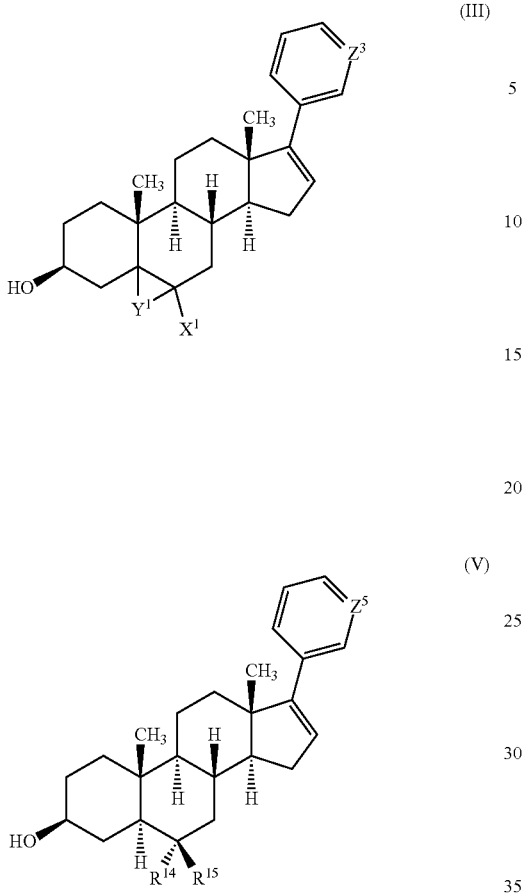

(V)

21. A compound according to formula I or II

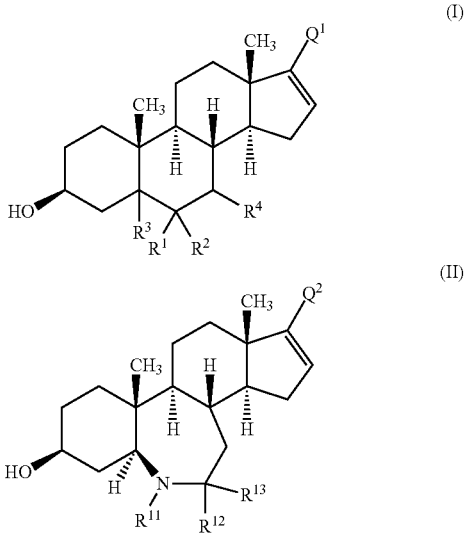

or a salt thereof, or a tautomer thereof, or a solvate thereof, wherein $Q^1$ and $Q^2$ are each independently

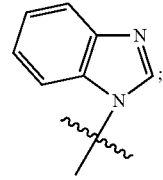 [SMILES: *n1cnc2ccccc21]

or a salt thereof, or a tautomer thereof, or a solvate thereof, wherein $X^1$ is H, $C(O)NR^{16}R^{17}$, $C(O)OR^{18}$, $NR^{19}R^{20}$, trifluoromethyl, halo, nitro, or cyano;

$Y^1$ is O, $NR^{21}$, S, S(O), $S(O)_2$, or a bond, provided that when $Y^1$ is not $NR^{21}$ or a bond then $X^1$ is not $NR^{19}R^{20}$;

$Z^3$ and $Z^5$ are each independently N;

$R^{14}$ and $R^{15}$ are each independently H, OH, $NR^{22}R^{23}$, trifluoromethoxy, or a substituted or unsubstituted alkoxy, aryloxy, arylalkoxy, or alkanoyloxy, group provided that $R^{14}$ and $R^{15}$ are not both H;

or $R^{14}$ and $R^{15}$ together are =O, =N—OH, or =N—NHR$^{24}$;

$R^{16}$, $R^{17}$, $R^{19}$, $R^{20}$, $R^{21}$, $R^{22}$, $R^{23}$, and $R^{24}$ are each independently H or a substituted or unsubstituted alkyl, cycloalkyl, cycloalkylalkyl, alkanoyl, aryl, aralkyl, heterocyclyl, heteroaryl, heterocyclylalkyl, or heteroaralkyl group; and $R^{18}$ is H or a substituted or unsubstituted alkyl, cycloalkyl, cycloalkylalkyl, aryl, aralkyl, heterocyclyl, heteroaryl, heterocyclylalkyl, or heteroaralkyl group;

with the proviso that when $Z^1$ is N and $Y^1$ is a bond then $X^1$ is not H.

20. The method of claim 16, wherein the method comprises parenterally administering the compound.

$R^1$ is H, OH, $C(O)NR^{27}R^5$, $C(O)OR^6$, $NR^7R^8$, trifluoromethyl, trifluoromethoxy, halo, nitro, cyano, or a substituted or unsubstituted alkoxy, aryloxy, arylalkoxy, or alkanoyloxy group, or $R^1$ and $R^2$ together are =O, =N—OH, or =N—NHR$^9$;

$R^2$ is OH, $C(O)NR^{27}R^5$, $C(O)OR^6$, $NR^7R^8$, trifluoromethyl, trifluoromethoxy, halo, nitro, cyano, or a substituted or unsubstituted alkoxy, aryloxy, arylalkoxy, or alkanoyloxy group;

$R^3$ is H, or $R^1$ and $R^3$ together are O, $NR^9$, S, S(O), $S(O)_2$, or a bond, provided that when $R^1$ and $R^3$ together are not $NR^9$ or a bond then $R^2$ is not $NR^7R^8$;

$R^4$ is H, or $R^1$ and $R^4$ together are O, $NR^{10}$, S, S(O), $S(O)_2$, or a bond, provided that when $R^1$ and $R^3$ together are not $NR^{10}$ or a bond then $R^2$ is not $NR^7R^8$;

$R^{27}$, $R^5$, $R^7$, $R^8$, $R^9$, and $R^{10}$ are each independently H or a substituted or unsubstituted alkyl, cycloalkyl, cycloalkylalkyl, alkanoyl, aryl, aralkyl, heterocyclyl, heteroaryl, heterocyclylalkyl, or heteroaralkyl group;

$R^6$ is independently at each occurrence H or a substituted or unsubstituted alkyl, cycloalkyl, cycloalkylalkyl, aryl, aralkyl, heterocyclyl, heteroaryl, heterocyclylalkyl, or heteroaralkyl group;

$R^{11}$ is H or a substituted or unsubstituted cycloalkyl, cycloalkylalkyl, alkanoyl, aryl, aralkyl, heterocyclyl, heteroaryl, heterocyclylalkyl, or heteroaralkyl group; and $R^{12}$ and $R^{13}$ are each H or together are =O, provided that $R^{12}$ and $R^{13}$ together are not =O when $R^{11}$ is H; or $R^{11}$, $R^{12}$, and $R^{13}$ together are —N=N—N=.

22. A compound according to formula I or II

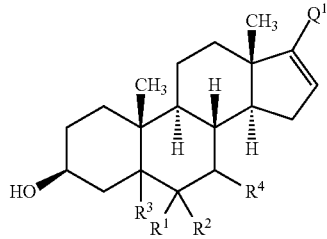
(I)

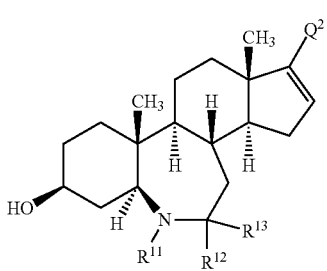
(II)

or a salt thereof, or a tautomer thereof, or a solvate thereof, wherein $Q^1$ and $Q^2$ are each independently

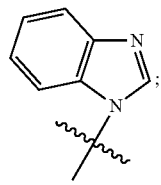 [SMILES: *n1cnc2ccccc21]

$R^1$ and $R^4$ together are O, $NR^{10}$, S, S(O), $S(O)_2$, or a bond;

$R^2$ is H, OH, $C(O)NR^{27}R^5$, $C(O)OR^6$, $NR^7R^8$, trifluoromethyl, trifluoromethoxy, halo, nitro, cyano, or a substituted or unsubstituted alkoxy, aryloxy, arylalkoxy, or alkanoyloxy group;

$R^3$ is H;

$R^{27}$, $R^5$, $R^7$, $R^8$, $R^9$, and $R^{10}$ are each independently H or a substituted or unsubstituted alkyl, cycloalkyl, cycloalkylalkyl, alkanoyl, aryl, aralkyl, heterocyclyl, heteroaryl, heterocyclylalkyl, or heteroaralkyl group;

$R^6$ is independently at each occurrence H or a substituted or unsubstituted alkyl, cycloalkyl, cycloalkylalkyl, aryl, aralkyl, heterocyclyl, heteroaryl, heterocyclylalkyl, or heteroaralkyl group;

$R^{11}$ is H or a substituted or unsubstituted cycloalkyl, cycloalkylalkyl, alkanoyl, aryl, aralkyl, heterocyclyl, heteroaryl, heterocyclylalkyl, or heteroaralkyl group; and $R^{12}$ and $R^{13}$ are each H or together are =O, provided that $R^{12}$ and $R^{13}$ together are not =O when $R^{11}$ is H; or $R^{11}$, $R^{12}$, and $R^{13}$ together are —N=N—N=.

* * * * *

UNITED STATES PATENT AND TRADEMARK OFFICE
CERTIFICATE OF CORRECTION

PATENT NO. : 9,611,270 B2  
APPLICATION NO. : 14/815686  
DATED : April 4, 2017  
INVENTOR(S) : Jeffrey Aube et al.

Page 1 of 1

It is certified that error appears in the above-identified patent and that said Letters Patent is hereby corrected as shown below:

In the Claims

In Claim 6, Column 58, Line 8:
Delete "$R^{1A}$" and insert --$R^{14}$-- therefore.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*